United States Patent [19]

Drucker

[11] Patent Number: 5,834,428
[45] Date of Patent: Nov. 10, 1998

[54] GLUCAGON-LIKE PEPTIDE-2 AND ITS THERAPEUTIC USE

[75] Inventor: Daniel J. Drucker, Toronto, Canada

[73] Assignee: 1149336 Ontario Inc., Toronto, Canada

[21] Appl. No.: 669,790

[22] Filed: Jun. 28, 1996

Related U.S. Application Data

[63] Continuation of Ser. No. 632,533, Apr. 12, 1996, which is a continuation-in-part of Ser. No. 422,540, Apr. 14, 1995.

[51] Int. Cl.$^6$ .................................................. A61K 38/00
[52] U.S. Cl. ................................... 514/12; 514/2; 514/3; 530/324; 530/303; 530/308; 435/366; 435/371; 935/52; 935/55; 935/66; 935/70; 935/71
[58] Field of Search ...................... 514/2, 3, 12; 530/324, 530/308, 303; 935/52, 55, 66, 70, 71; 435/366, 371

[56] References Cited

FOREIGN PATENT DOCUMENTS 612531  8/1994  European Pat. Off. ..

OTHER PUBLICATIONS

Barragan, J.M.; Rodriguez, R.E.; and Blazquez, E. Changes in arterial blood pressure and heart rate induced by glucagon–like peptide–1–(7–36) amide in rats. *American Journal of Physiology.* 266 (3 Pt 1), pE459–66, Mar. 1994.

Bloom, S.R. Gut Hormones in adaption. *Gut.* 28, S1, pp. 31–35, 1987.

Brubaker, Patricia L. Regulation of Intestinal Proglucagon–Derived Peptide Secretion by Intestinal Regulatory Peptides. *Endocrinology.* vol. 128, No. 6, pp. 3175–3182, 1991.

Buhl, Thora; Thim, Lars; Kofod, Hans; Orskov, Catherine; Harling, Henrik; and Holst, Jens. J. Naturally Occurring Products of Proglucagon 111–160 in the Porcine and Human Small Intestine. *The Journal of Biology Chemistry.* vol. 263, No. 18, pp. 8621–8624, Issue of Jun. 25, 1988.

Calvo, J.C.; Yusta, B; Mora, F; and Blazquez, E. Structural characterization by affinity cross–linking of glucagon–like peptide–1 (7–36) amide receptor in rat brain. *J. Neurochem.* 64(1), pp. 299–306, Jan. 1995.

Cheeseman, Chris I.; and Raymand Tsang. The effect of gastric inhibitory polypeptide and glucagon like peptides on intestinal basolateral membrane hexose transport. *The American Physiological Society.* APSracts 3:0071G, Apr. 1996.

Drucker. *Pancreas.* 1990, 5(4):484.

Ehrlich, Peter; Tucker, Devin; Asa, Sylvia L.; Brubacker, Patricia L.; and Drucker, Daniel J. Inhibition of pancreatic proglucagon gene expression in mice bearing subcutaneous endocrine tumors. *American Journal of Physiology.* pp. E662–E671, 1994.

George, S.K.; Uttenthal, L.O.; Ghiglione, M.; and Bloom, S.R. Molecular forms of glucagon–like peptides in man. *FEBS Letters.* vol. 192, No. 2, pp. 275–278, Nov. 1985.

Hoosein, Naseema M.; and Gurd, Ruth S. Human glucan–like peptides 1 and 2 activate rat brain adenylate cyclase. *FEBS Letters.* vol 178, No. 1, pp. 83–86, Dec. 1984.

Irwin, David M.; and Wong, Jaffe. Trout and Chicken Proglucagon: Alternative Splicing Generates mRNA Transcripts Encoding Glucagon–Like Peptide 2. *Molecular Endocrinology.* 9:267–277, 1995.

Lee, Ying C.; Asa, Sylvia L.; and Drucker, Daniel J. Glucagon Gene 5"–Flanking Sequences Direct Expression of Simian Virus 40 Large T Antigen to the Intestine, Producing Carcimona of the Large Bowel in Transgenic Mice. *The Journal of Biological Chemistry.* vol. 267, No. 15, pp. 10706–10708, May 25, 1992.

Lund, P. Kay; Hoyt, Eileen; Simmons, James G.; and Ulshen, Martin H. Regulation of Intestinal Glucagon Gene Expression during Adaptive Growth of Small Intestine. *Digestion.* 54:371–373, 1993.

Mojsov, Svetlana; Heinrich, Richard; Wilson, Ira B.; Ravazzola, Mariella; Orci, Lelio; and Habener, Joel F. Preproglucagon Gene Expression in Pancreas and Intestine Diversifies at the Level of Post–translational Processing. *The Journal of Biological Chemistry.* vol. 261, No. 25, pp. 11880–11889, Sep. 5, 1986.

Mommsen, Thomas P.; Andrews, P.C.; and Plisetskaya, Erika M. Glucagon–like peptides activate hepatic gluconeogenesis. *FEBS Letters.* vol. 219, No. 1, pp. 227–232, Jul. 1987.

Nishi and Steiner, *Mol. Endocrinol.,* 1990, 4:1192–8.

Orskov, C.; Buhl, T.; Rabenhoj, L.; Kofod, H.; and Holst, J.J.. Carboxpeptidase–B–like processing of the C–terminus of glucagon–like peptide–2 in pig and human small intestine. *FEBS Letters.* 247(2), pp. 193–196, Apr. 24, 1989.

Orskov, C.; Holst, J.J.; Pouisen, S. Seier; and Kirkegaard, P. Pancreatic and intestinal processing of proglucagon in man. *Diabetologia.* 30:874–881, 1987.

Orskov, C; and Holst, J.J. Radio–immunassays for glucagon–like peptides 1 and 2 (GLP–1 and GLP–2). *Scand. J. Clin. Lab. Invest.* 47(2), pp. 165–174, Apr. 1987.

Orskov, Catherine; Holst, Jens J.; Knuhtsen, Svend; Baldissera, Furio G.A.; Poulsen, Steen S.; and Nielsen, O. Vagn. Glucagon–Like Peptides GLP–1 and GLP–2, Predicted Products of the Glucagon Gene, Are Secreted Separately from Pig Small Intestine but Not Pancreas. *Endocrinology.* vol. 119, No. 4, pp. 1467–1475, 1986.

Ruiz–Grand, C.; Pintado, J.; Alarcon, C.; Castilla, C.; Valverde, I; Lopez–Novoa, J.M. Renal catabolism of human glucagon–like peptides 1 and 2. *Can. J. Physiol. Pharmacol.* 68 (12), pp. 1568–1573, Dec. 1990.

Shennan, K.I.J.; and Docherty, K. Proglucagon expression, posttranslational processing and secretion in SV40–transformed islet cells. *Molecular and Cellular Endocrinology.* 67(1989), pp. 93–99.

*Primary Examiner*—Sheela Huff
*Attorney, Agent, or Firm*—Pennie & Edmonds LLP

[57] ABSTRACT

Glucagon-like peptide 2, a product of glucagon gene expression, and analogs of glucagon-like peptide 2, have been identified as gastrointestinal tissue growth factors. Their effects on the growth of small bowel and pancreatic islets are described. Their formulation as a pharmaceutical, and their therapeutic use in treating disorders of the bowel, are described.

16 Claims, 14 Drawing Sheets

OTHER PUBLICATIONS

Watanabe, Nobuaki; Matsuyama, Tatsuo; Namba, Mitsuyoshi; Miyagawa, Jun–ichiro; Itoh, Hidehiko; Komatsu, Ryoya; Kono, Norio; and Tarui, Seiichiro. Trophic Effect of Glucagon–(1–21)–Peptide on the Isolated Rat Ileal Mucosal Cells. *Biochemical and Biophysical Research Communications.* vol. 152, No. 3, pp. 1038–1044, May 16, 1988.

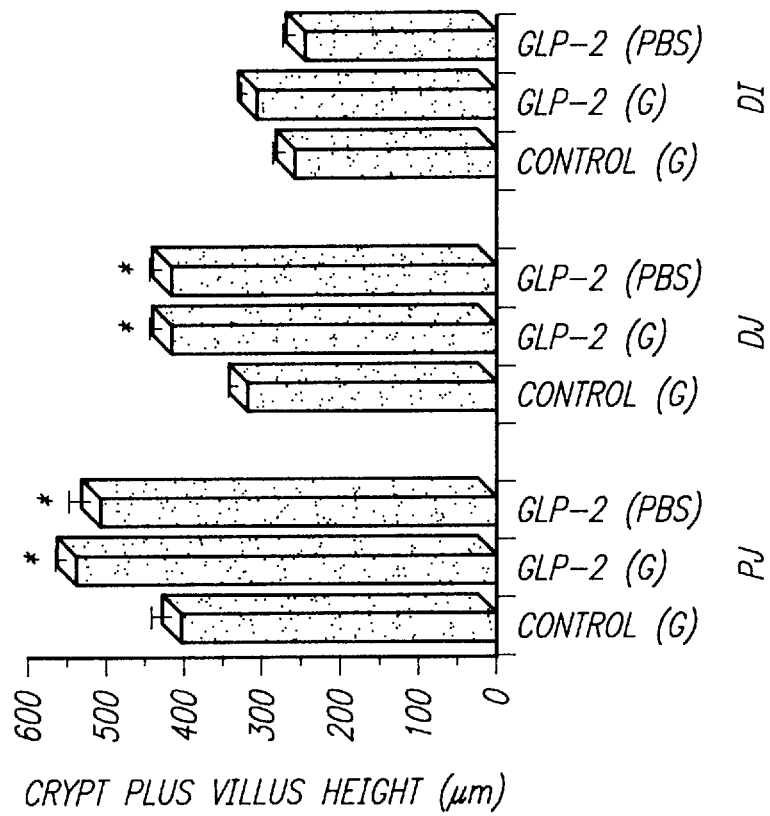
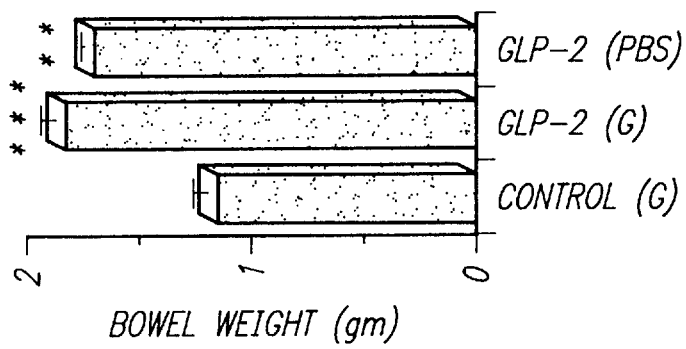

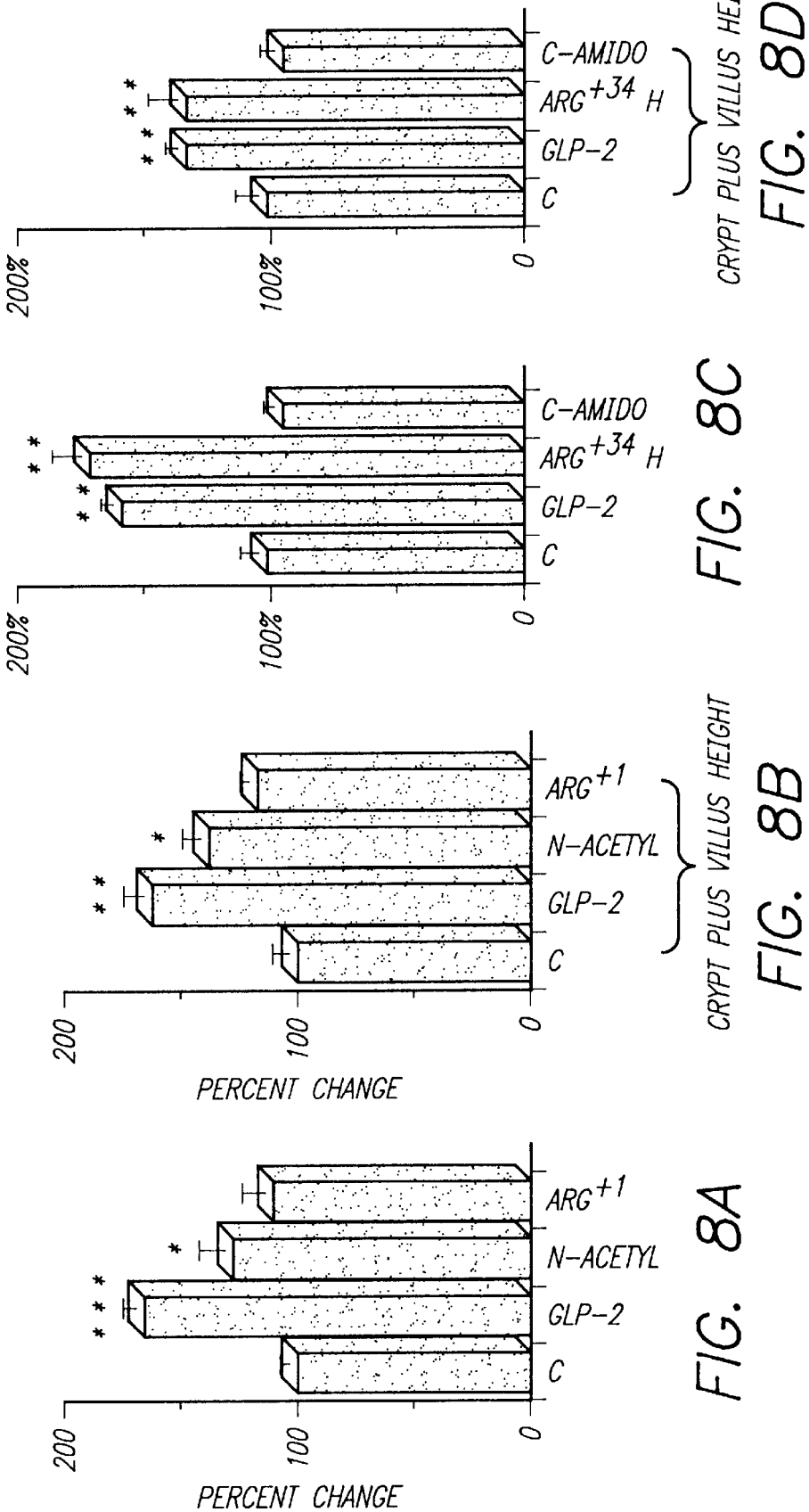

GLUCAGON-LIKE PEPTIDE-2 AND ITS THERAPEUTIC USE

CROSS-REFERENCE TO RELATED APPLICATIONS

This application is a continuation of application Ser. No. 08/632,533, filed Apr. 12, 1996 which is a continuation-in-part of application Ser. No. 08/422,540, filed Apr. 14, 1995, the disclosures of which are incorporated by reference herein.

FIELD OF THE INVENTION

This invention relates to glucagon-related peptides having gastrointestinal tissue growth-promoting properties, and to their use therapeutically to treat various medical conditions resulting from the impaired growth or loss of gastrointestinal tissue, particularly intestinal and pancreatic tissue.

BACKGROUND TO THE INVENTION

Expression of the glucagon gene yields a tissue-specific variety of peptide products that are processed from the 160 residue proglucagon product. The organization of these peptides within the proglucagon precursor was elucidated by the molecular cloning of preproglucagon cDNAs from the anglerfish, rat, hamster and bovine pancreas. These analyses revealed that preproglucagon contains not only the sequence of glucagon and glicentin, but also two additional glucagon-like peptides (GLP-1 and GLP-2) separated from glucagon and each other by two spacer or intervening peptides (IP-I and IP-II). These peptides are flanked by pairs of basic amino acids, characteristic of classic prohormone cleavage sites, suggesting they might be liberated after posttranslational processing of proglucagon (Drucker, Pancreas, 1990, 5(4):484).

Analysis of the peptides liberated from proglucagon in the pancreatic islets of Langerhans, for instance, suggests the primary pancreatic peptide liberated is the 29-mer glucagon, whereas glicentin, oxyntomodulin, IP-II and the glucagon-like peptides are more prevalent in the small and large intestines. This demonstration that the glucagon-like peptides are found in the intestine has prompted research into the precise structure and putative function(s) of these newly discovered gut peptides. Most studies have focussed on GLP-1, because several lines of evidence suggested that GLP-1 may be an important new regulatory peptide. Indeed, it has been determined that GLP-1 is the most potent known peptidergic stimulus for insulin release, an action mediated in a glucose-dependent manner through interaction with receptors on pancreatic β cells. GLP-1 and its derivatives are in development for use in the treatment of diabetics.

The physiological roles of glicentin and oxyntomodulin, the so-called "enteroglucagons", are also under investigation, particularly with respect to regulation of acid secretion and the growth of intestinal cells. oxyntomodulin is capable of inhibiting pentagastrin-stimulated gastric acid secretion in a dose-dependent manner. The role of glicentin in mediating the changes of intestinal adaptation and growth of the intestinal mucosa has been investigated, and the intestinotrophic effect of glicentin and its therapeutic use have been reported by Matsuno et al in EP 612,531 published Aug. 31, 1994.

In contrast to GLP-1 and other glucagon-related peptides, the physiological role of glucagon-like peptide (GLP-2) remains poorly understood despite the isolation and sequencing of various GLP-2 homologues from human, rat, bovine, porcine, guinea pig, hamster, and degu species. Using GLP-2 antisera raised against synthetic versions of GLP-2, various groups have determined that GLP-2 is present primarily in intestinal rather than pancreatic extracts (see Mojsov et al, J. Biol. Chem., 1986, 261(25):11880; Orskov et al in Endocrinology, 1986, 119(4):1467 and in Diabetologia, 1987, 30:874 and in FEBS Letters, 1989, 247(2):193; George et al, FEBS Letters, 1985, 192(2):275). With respect to its biological role,. Hoosein et al report (FEBS Letters, 1984, 178(1):83) that GLP-2 neither competes with glucagon for binding to rat liver and brain tissues, nor stimulates adenylate cyclase production in liver plasma membranes, but, enigmatically, can stimulate adenylate cyclase in both rat hypothalamic and pituitary membranes at 30–50 pM concentrations. An elucidation of the physiological role of GLP-2 would clearly be desirable.

SUMMARY OF THE INVENTION

It has now been determined that GLP-2 acts as a trophic agent, to promote growth of gastrointestinal tissue. The effect of GLP-2 is marked particularly by increased growth of the small bowel, and is therefore herein referred to as an "intestinotrophic" effect. Remarkably, the growth promoting effects of GLP-2 also manifest as pancreatic islet growth, and particularly by enlargement and proliferation of the islets. It is accordingly a general object of the present invention to exploit GLP-2 and GLP-2 analogs for therapeutic and related purposes.

More particularly, and according to one aspect of the invention, there is provided a GLP-2 or a GLP-2 analog in a pharmaceutically acceptable form that is suitable for formulation and subsequent administration to patients.

In another of its aspects, the invention provides a pharmaceutical composition comprising a GLP-2 or a GLP-2 analog and a pharmaceutically acceptable carrier.

In a further aspect, the invention provides a method for promoting the growth and proliferation of gastrointestinal tissue, including small bowel and pancreatic islet tissue, in a patient in need thereof, comprising the step of delivering to the patient a gastrointestinal tissue growth-promoting amount of a GLP-2 or a GLP-2 analog.

In another aspect of the invention, there is provided a method useful to identify novel intestinotrophic GLP-2 analogs, comprising the steps of:

1) obtaining an analog of an intestinotrophic GLP-2, the analog having at least one amino acid substitution, deletion, addition, or an amino acid with a blocking group;

2) treating a mammal with said analog using a regimen capable of eliciting an intestinotrophic effect when utilized for rat GLP-2; and 3) determining the effect of said analog on small bowel weight and/or on the crypt plus villus height and/or pancreatic islet size relative to a mock treated control mammal,whereby said intestinotrophic peptide is identified as an analog which elicits an increase in said weight and/or said height and/or said size.

In another of its aspects, the present invention provides novel GLP-2 analogs, in the form of intestinotrophic analogs of vertebrate GLP-2's. These GLP-2 analogs promote growth and proliferation of gastrointestinal tissue, including small bowel tissue and pancreatic islet tissue.

In another aspect of the invention, there is provided a method in which treatment of patients to restore gastrointestinal tissue is performed by the steps of (1) culturing said tissue or cells therefrom with a tissue growth promoting amount of a GLP-2, or a GLP-2 analog, and then (2) implanting the said tissue or cells in the patient to be treated.

In a related aspect, the invention provides a method for growing gastrointestinal tissue or cells therefrom, which comprises the step of culturing the said tissue or cells in a culturing medium supplemented with a growth promoting amount of a GLP-2 or a GLP-2 analog.

BRIEF REFERENCE TO THE DRAWINGS

FIGS. 1(A–D) illustrates dose-response results with a GLP-2. Measurements of the effect on small bowel weight (BW-panel A), crypt plus villus height in proximal jejunum (PJ-panel B), distal jejunum (DJ-panel C), and distal ileum (DI-panel D) in animals injected with rat GLP-2, are each plotted as a function of rat GLP-2 dose.

FIGS. 2(A–D) illustrates the effect of formulation vehicle on the intestinotrophic activity of a GLP-2. Small bowel weight (BW), and crypt plus villus height in proximal jejunum (PJ), distal jejunum (DJ), and distal ileum (DI) were each measured as a function of administration of rat GLP-2 in gelatin (G) or saline (PBS). A gelatin solution without rat GLP-2 was used as a control (C).

FIG. 3 illustrates the effect of administration route on the intestinotrophic activity of a GLP-2. The percentage change in small bowel weight was measured after rat GLP-2 was injected either sub-cutaneously (SC), intramuscularly (IM), or intraperitoneally (IP). Bars marked with T indicates samples from rats treated with GLP-2; C indicates samples obtained from control rats injected with saline.

FIG. 4 illustrates the effect of administration frequency on GLP-2 activity. Animals were injected subcutaneously with PBS every 12 hours, with 2.5 μg rat GLP-2 every 12 hours (q12h), with 5 μg rat GLP-2 each day (qd), or with 10 μg rat GLP-2 every other day (qod), as indicated on the x-axis. Small bowel weight (BW), and crypt plus villus height in proximal jejunum (PJ), distal jejunum (DJ), and distal ileum (DI) were measured for each administration protocol.

FIGS. 5(A–C) illustrates the effect of duration of GLP-2 administration as a function of activity. Animals were injected once every day with 5 μg of rat GLP-2 in 10% gelatin, or with 10% gelatin alone for four weeks (panel A), eight weeks (panel B), or 12 weeks (panel C), then sacrificed. The effect of treatment with GLP-2 relative to the control was measured for small bowel weight (BW), and crypt plus villus height in proximal jejunum (PJ), distal jejunum (DJ), and distal ileum (DI).

FIG. 6 provides a time course of the intestinotrophic effect of a GLP-2. Female mice injected twice daily with 2.5 μg of rat GLP-2 in PBS were sacrificed at various days after initiation of treatment, and small bowel weight was assessed relative to a control animal injected with PBS alone.

FIGS. 7-1(A–D) and 7-2(E–H) illustrate recipient age and gender effects on the intestinotrophic activity of GLP-2. In panels A through H, sex matched GLP-2 treated animals (CD1 mice) from 4 to 16 weeks of age were compared to their own controls for both small bowel weight (BW) and crypt plus villus height in proximal jejunum (PJ), distal jejunum (DJ), and distal ileum (DI) after treatment with rat GLP-2.

FIGS. 8(A–G) illustrates the intestinotrophic effect of a number of different GLP-2's and GLP-2 analogues relative to a control. Panels A, C, E, and G present change in small bowel weight (BW); Panel B, D, and F present change in crypt plus villus height in proximal jejunum (PJ). Analogue abbreviations are N-acetyl (rat GLP-2 peptide blocked at the amino terminus with an acetyl group), $Arg^{+1}$ (rat GLP-2 containing an additional Arg residue at the amino terminus), $Arg^{+34}$ (rat GLP-2 containing an additional Arg residue at the carboxyl terminus), C-amido (rat GLP-2 with an amido group blocking the carboxyl terminus), $Arg^{+1+2}$ containing two additional Arg residues at the amino terminus). Additionally, the effect of degu GLP-2 (degu) was tested for its intestinotrophic effect on mice.

FIG. 9 illustrates the intestinotrophic effect of rat GLP-2 on small bowel length. The increase in small bowel length is measured relative to a control animal after treatment with GLP-2 for 10 days.

DETAILED DESCRIPTION OF THE INVENTION

Figure 1A:
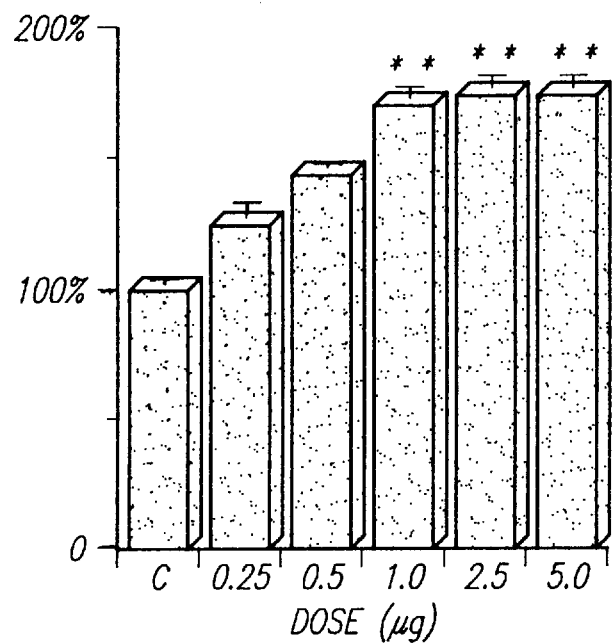
Figure 1B:
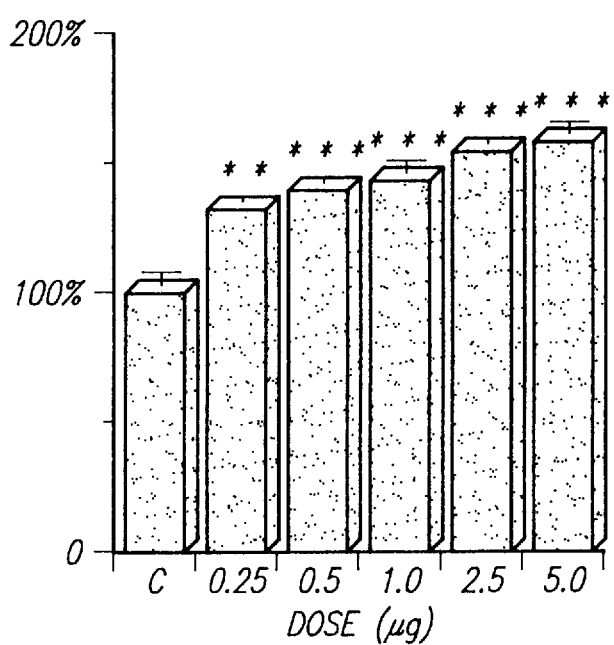
Figure 1C:
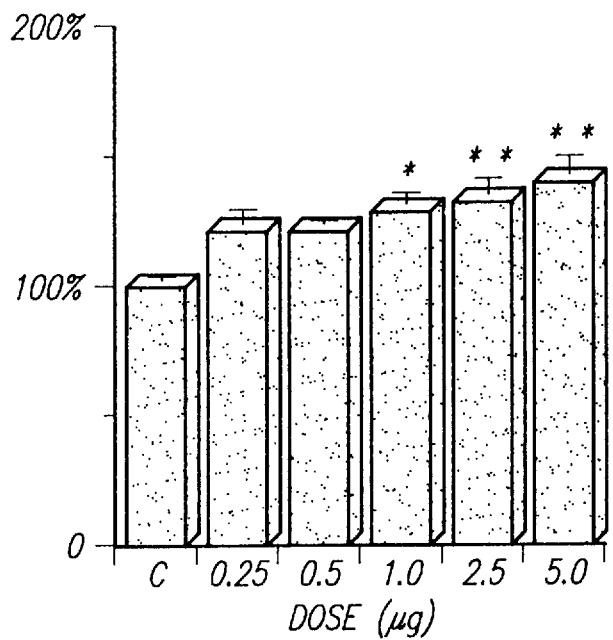
Figure 1D:
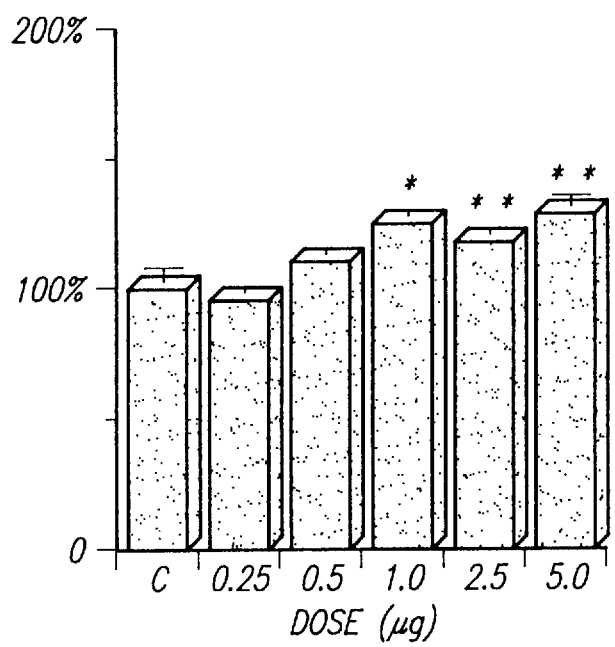

The invention relates to therapeutic and related uses of GLP-2 and GLP-analogs, particularly for promoting the growth and proliferation of gastrointestinal tissue, most particularly small bowel tissue or pancreatic islets. With respect to small bowel tissue, such growth is measured conveniently as a GLP-2-mediated increase in small bowel mass and length, relative to an untreated control. As demonstrated by the results presented herein, the effect of GLP-2 on small bowel also manifests as an increase in the height of the crypt plus villus axis. Such activity is referred to herein as an "intestinotrophic" activity. Also detectable in response to GLP-2 is an increase in crypt cell proliferation and/or a decrease in small bowel epithelium apoptosis. These cellular effects are noted most significantly in relation to the jejunum, including the distal jejunum and particularly the proximal jejunum, and are also noted in the distal ileum. A compound is considered to have "intestinotrophic effect" if test animals of at least one vertebrate species which responds to a reference GLP-2 peptide exhibit significantly increased small bowel weight, increased height of the crypt plus villus axis, or increased crypt cell proliferation or decreased small bowel epithelium apoptosis when treated with the compound (or genetically engineered to express it themselves).

A model suitable for determining such gastrointestinal growth is described by Matsuno et al, supra, and is exemplified below in Example 1. Morphometric analysis of the cellular effects of GLP-2 and GLP-2 analogs on the height of the crypt plus villus axis in small intestine is described below in Example 2.

With respect to pancreatic islets, such growth is revealed by GLP-2-mediated enlargement and/or proliferation of pancreatic islets, relative to an untreated control. A method of determining the intestinotrophic effect of a compound by assessing the effect of the test compound on pancreatic islet cell growth, including both increased size and numbers of pancreatic cells, is exemplified below in Example 1.

The term "GLP-2 peptide" refers collectively herein to GLP-2 which is naturally occurring in vertebrates, and to analogs of naturally occurring forms of GLP-2, which GLP-2 analogs elicit an intestinotrophic effect and are structurally altered, relative to a given vertebrate GLP-2, by at least one amino acid addition, deletion, substitution, or by incorporation of an amino acid(s) with a blocking group.

The various vertebrate forms of GLP-2 include, for example, rat GLP-2 and its homologues including ox GLP-2, porcine GLP-2, degu GLP-2, bovine GLP-2, guinea pig GLP-2, hamster GLP-2, human GLP-2, rainbow trout GLP-2, and chicken GLP-2, the sequences of which have been reported by many authors including Buhl et al in J. Biol. Chem., 1988, 263(18):8621, Nishi and Steiner, Mol. Endocrinol., 1990, 4:1192–8, and Irwin and Wong, Mol.

Endocrinol., 1995, 9(3):267–77. The sequences reported by these authors is incorporated herein by reference.

Analogs of vertebrate GLP-2 can be generated using standard techniques of peptide chemistry and can be assessed for intestinotrophic activity, all according to the guidance provided herein. Particularly preferred analogs of the invention are those based upon the sequence of human GLP-2, as follows:

His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:4)

wherein one or more amino acid residues are conservatively substituted for another amino acid residue, as long as the analog still maintains intestinotrophic activity, such as small bowel growth, pancreatic islet growth, and/or increase in crypt/villus height, in a vertebrate.

Conservative substitutions in any naturally occurring GLP-2, preferably the human GLP-2 sequence, are defined as exchanges within any of the following five groups:

I. Ala, Ser, Thr, Pro, Gly

II. Asn, Asp, Glu, Gln

III. His, Arg, Lys

IV. Met, Leu, Ile, Val, Cys

V. Phe, Tyr, Trp.

The invention also encompasses non-conservative substitutions of amino acids in any vertebrate GLP-2 sequence, provided that the non-conservative substitutions occur at amino acid positions known to vary in GLP-2 isolated from different species. Non-conserved residue positions are readily determined by aligning all known vertebrate GLP-2 sequences. For example, Buhl et al., J. Biol. Chem., 1988, 263(18):8621, compared the sequences of human, porcine, rat, hamster, guinea pig, and bovine GLP-2's, and found that positions 13, 16, 19, 27 and 28 were non-conserved (position numbers refer to the analogous position in the human GLP-2 sequence). Nishi and Steiner, Mol. Endocrinol., 1990, 4:1192–8, found that an additional position within the sequence encoding GLP-2, residue 20 in the above human sequence, also varied in degu, a rodent species indigenous to South America. Thus, under this standard, the amino acid positions which vary in mammals and which preferably may be substituted with non-conservative residues are positions 13, 16, 19, 20, 27, and 28. The additional amino acid residues which vary in vertebrates and which also may be substituted with non-conserved residues occur at positions 2, 5, 7, 8, 9, 10, 12, 17, 21, 22, 23, 24, 26, 29, 30, 31, 32, and 33.

Alternatively, non-conservative substitutions may be made at any position in which alanine-scanning mutagenesis reveals some tolerance for mutation in that substitution of an amino acid residue with alanine does not destroy all intestinotrophic activity. The technique of alanine scanning mutagenesis is described by Cunningham and Wells, Science, 1989, 244:1081, and incorporated herein by reference in its entirety. Since most GLP-2 sequences consist of only approximately 33 amino acids (and in human GLP-2 alanine already occurs at four positions), one of skill in the art could easily test an alanine analogue at each remaining position for intestinotrophic effect, as taught in the examples below.

By aligning the known sequences of vertebrate GLP-2, a general formula has been constructed which takes into account the significant sequence homology among these GLP-2 species, as well as the residues which are known to vary between species. This formula may be used to guide the choice of particular preferred non-conserved residues for substitution, addition, deletion, or modification by addition of amino acid blocking groups. Thus, particular analogs of vertebrate GLP-2 embraced by the present invention, in accordance with one of its aspects, are those vertebrate GLP-2's and GLP-2 analogs that conform to the general formula represented below as SEQ ID NO:1

R1-[Y]m-His-Ala-Asp-Gly-Ser-Phe-Ser-Asp-Glu-Met-AsnThr-aa1-Leu-Asp-aa2-Leu-Ala-aa3-aa4-Asp-Phe-Ile-Asn-Trp-Leu-aa5-aa6-Thr-Lys-Ile-Thr-Asp-[X]n-R2 wherein aa refers to any amino acid residue, and aa1 through aa6 are those residue positions known to vary among GLP-2 sequences obtained from different species, and:

X is one or two amino acids selected from group III, such as Arg, Lys or Arg-Arg Y is one or two amino acids selected from group III, such as Arg, Lys or Arg-Arg m is 0 or 1;

n is 0 or 1;

R1 is H or an N-terminal blocking group; and

R2 is OH or a C-terminal blocking group.

In several of the embodiments of the invention, aa1 through aa6 are as defined below:

aa1 is selected from group IV;

aa2 is selected from group I or II;

aa3 is selected from group I;

aa4 is selected from group III;

aa5 is selected from group IV;

aa6 is selected from group II or III.

In particularly preferred embodiments of the invention, aa1 through aa6 are chosen from the group of residues which are known to occur at that position in GLP-2's isolated from different species, as follows:

aa1 is Ile or Val;

aa2 is Asn or Ser;

aa3 is Ala or Thr;

aa4 is Lys or Arg;

aa5 is Ile or Leu; and aa6 is Gln or His.

Human and rat GLP-2 differ from one another at only the amino acid residue at position 19. In the human sequence, this residue is alanine; in rat GLP-2, position 19 is threonine. Thus, particular GLP-2 or GLP-2 analogs embraced by the invention contain a variable residue at position 19. In these embodiments of the invention, the GLP-2 peptide conforms to SEQ ID NO:2 shown below:

R1-[Y]m-His-Ala-Asp-Gly-Ser-Phe-Ser-Asp-Glu-Met-AsnThr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 wherein aa3, Y, m, X, n, R1 and R2 are as defined above.

In specific embodiments of the invention, the GLP-2 peptide is selected from 1) rat GLP-2 having SEQ ID NO:3 illustrated below:

His-Ala-Asp-Gly-Ser-Phe-Ser-Asp-Glu-Met-Asn-Thr-Ile-Leu-Asp-Asn-Leu-Ala-Thr-Arg-Asp-Phe-Ile-Asn-Trp-Leu-Ile-Gln-Thr-Lys-Ile-Thr-Asp (SEQ ID NO:3);

2) human GLP-2, which is the Thr$^{19}$ to Ala$^{19}$ equivalent of rat GLP-2 illustrated below:

His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp(SEQ ID NO:4)

3) degu GLP-2 which is the [Ile$^{13}$ to Val$^{13}$, Asn$^{16}$ to His$^{16}$, Lys$^{20}$ to Arg$^{20}$] equivalent of rat GLP-2; and 4) GLP-2's, and GLP-2 analogs, which incorporate an N-terminal blocking group and/or an N-terminal extension such as Arg or Arg-Arg; and/or incorporate a C-terminal blocking group and/or a C-terminal extension such as Arg or Arg-Arg.

The "blocking groups" represented by R1 and R2 are chemical groups that are routinely used in the art of peptide chemistry to confer biochemical stability and resistance to digestion by exopeptidase. Suitable N-terminal protecting groups include, for example, $C_{1-5}$-alkanoyl groups such as acetyl. Also suitable as N-terminal protecting groups are amino acid analogues lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$alkyl groups, e.g., methyl, ethyl and propyl groups, while amide-forming groups include amino functions such as primary amine, or alkylamino functions, e.g., mono-$C_{1-5}$alkylamino and di-$C_{1-5}$alkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine.

The particular form of GLP-2 selected for promoting the growth of gastrointestinal tissue can be prepared by a variety of techniques well known for generating peptide products. Vertebrate forms of GLP-2 can of course be obtained by extraction from the natural source, using an appropriate combination of protein isolation techniques. As described by Buhl et al, supra, porcine GLP-2 isolation and purification is achieved from acid-ethanol extracts of ileal mucosa by a combination of size selection and HPLC-based fractionation, with the aid of antibody raised against synthetic proglucagon 126–159, to monitor work-up. As an alternative to GLP-2 extraction, those forms of GLP-2 that incorporate only L-amino acids, whether vertebrate GLP-2 or analogs thereof, can be produced in commercial quantities by application of recombinant DNA technology. For this purpose, DNA coding for the desired GLP-2 or GLP-2 analog is incorporated into an expression vector and transformed into a microbial, e.g., yeast, or other cellular host, which is then cultured under conditions appropriate for GLP-2 expression. A variety of gene expression systems have been adapted for this purpose, and typically drive expression of the desired gene from expression controls used naturally by the chosen host. Because GLP-2 does not require post translational glycosylation for its activity, its production may most conveniently be achieved in bacterial hosts such as *E. coli*. For such production, DNA coding for the selected GLP-2 peptide may usefully be placed under expression controls of the lac, trp or PL genes of *E. coli*. As an alternative to expression of DNA coding for the GLP-2 per se, the host can be adapted to express GLP-2 peptide as a fusion protein in which the GLP-2 is linked releasably to a carrier protein that facilitates isolation and stability of the expression product.

In an approach universally applicable to the production of a selected GLP-2 or GLP-2 analog, and one used necessarily to produce GLP-2 peptides that incorporate non-genetically encoded amino acids and N- and C-terminally derivatized forms, the well established techniques of automated peptide synthesis are employed, general descriptions of which appear, for example, in J. M. Stewart and J. D. Young, *Solid Phase Peptide Synthesis*, 2nd Edition, 1984, Pierce Chemical Company, Rockford, Ill.; and in M. Bodanszky and A. Bodanszky, *The Practice of Peptide Synthesis*, 1984, Springer-Verlag, New York; Applied Biosystems 430A Users Manual, 1987, ABI Inc., Foster City, Calif. In these techniques, GLP-2 peptide is grown from its C-terminal, resin-conjugated residue by the sequential addition of appropriately protected amino acids, using either the Fmoc or tBoc protocols, as described for instance by Orskov et al, 1989, supra.

For the incorporation of N- and/or C- blocking groups, protocols conventional to solid phase peptide synthesis methods can also be applied. For incorporation of C-terminal blocking groups, for example, synthesis of the desired peptide is typically performed using, as solid phase, .a supporting resin that has been chemically modified so that cleavage from the resin results in a GLP-2 peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxybenzyl alcohol or equivalent linker, can be used for this purpose, with cleavage from the support being effected by TFA in dichloromethane. Esterification of the suitably activated carboxyl function, e.g., with DCC, can then proceed by addition of the desired alcohol, followed by deprotection and isolation of the esterified GLP-2 peptide.

Incorporation of N-terminal blocking groups can be achieved while the synthesized GLP-2 peptide is still attached to the resin, for instance by treatment with suitable anhydride and nitrile. To incorporate an acetyl blocking group at the N-terminus, for instance, the resin-coupled peptide can be treated with 20% acetic anhydride in acetonitrile. The N-blocked GLP-2 peptide can then be cleaved from the resin, deprotected and subsequently isolated.

Once the desired GLP-2 peptide has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g., $C_4$-, $C_8$-, or $C_{18}$- silica. Such column fractionation is generally accomplished by running linear gradients, e.g., 10–90%, of increasing % organic solvent, e.g., acetonitrile, in aqueous buffer, usually containing a small amount (e.g., 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the GLP-2 peptide is then treated in the established manner to exchange the cleavage acid (e.g., TFA) with a pharmaceutically acceptable acid, such as acetic, hydrochloric, phosphoric, maleic, tartaric, succinic and the like, to generate a pharmaceutically acceptable acid addition salt of the peptide.

For administration to patients, the GLP-2 peptide or its salt is provided, in one aspect of the invention, in pharmaceutically acceptable form, e.g., as a preparation that is sterile-filtered, e.g., through a 0.22 µ filter, and substantially pyrogen-free. Desirably, the GLP-2 peptide to be formulated migrates as a single or individualized peak on HPLC, exhibits uniform and authentic amino acid composition and sequence upon analysis thereof, and otherwise meets standards set by the various national bodies which regulate quality of pharmaceutical products.

For therapeutic use, the chosen GLP-2 or GLP-2 analog is formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, e.g., when used as liquid nutritional supplements for patients on total parenteral nutrition therapy, or by injection, e.g., subcutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of the GLP-2 or GLP-2 analog may be enhanced, if desired, by incorporating a solubility enhancer, such as acetic acid.

The aqueous carrier or vehicle can be supplemented for use as injectables with an amount of gelatin that serves to depot the GLP-2 or GLP-2 analog at or near the site of injection, for its slow release to the desired site of action. Concentrations of gelatin effective to achieve the depot effect are expected to lie in the range from 10–20%. Alternative gelling agents, such as hyaluronic acid, may also be useful as depoting agents.

The GLP-2's and GLP-2 analogs of the invention may also be formulated as a slow release implantation device for extended and sustained administration of GLP-2. Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279-292 (1992). Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical Sciences," M. Dekker, New York, 1990. Liposomes may also be used to provide for the sustained release of a GLP-2 or GLP-2 analog. Details concerning how to use and make liposomal formulations of drugs of interest can be found in, among other places, U.S. Pat. No. 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of a GLP-2 or GLP-2 analog, e.g., near the pancreas to promote pancreatic growth, in diabetes, etc.

For use in stimulating growth of either small bowel or proliferation and increase of pancreatic islet cells in a mammal including a human, the present invention provides in one of its aspects a package, in the form of a sterile-filled vial or ampoule, that contains a tissue growth promoting amount of the GLP-2 or GLP-2 analog, in either unit dose or multi-dose amounts, wherein the package incorporates a label instructing use of its contents for the promotion of such growth. In one embodiment of the invention, the package contains the GLP-2 or GLP-2 analog and the desired carrier, as an administration-ready formulation. Alternatively, and according to another embodiment of the invention, the package provides the GLP-2 or GLP-2 analog in a form, such as a lyophilized form, suitable for reconstitution in a suitable carrier, such as phosphate-buffered saline.

In one embodiment, the package is a sterile-filled vial or ampoule containing an injectable solution which comprises an effective, intestinotrophic amount of GLP-2 or GLP-2 analog dissolved in an aqueous vehicle.

As an alternative to injectable formulations, the GLP-2 or GLP-2 analog may be formulated for administration by other routes. Oral dosage forms, such as tablets, capsules and the like, can be formulated in accordance with standard pharmaceutical practice.

According to the present invention, the GLP-2 or GLP-2 analog is administered to treat patients that would benefit from gastrointestinal tissue growth. In one aspect, patient candidates are those who would benefit from growth of small bowel tissue. The effects of GLP-2 peptide on this tissue, as evidenced by the results exemplified herein, is dramatic and would clearly benefit those patients suffering from diseases or conditions marked by abnormalities in the small intestinal tract mucosa, including: ulcers and inflammatory disorders; congenital or acquired digestion and absorption disorders including malabsorption syndromes; and diseases and conditions caused by loss of bowel mucosal function particularly in patients undergoing extended parenteral feeding or who, as a result of surgery, have undergone resection of the bowel and suffer from short-gut syndrome and cul-de-sac syndrome. Therapeutic treatment with GLP-2 peptides is administered so as to reduce or eliminate the disease symptoms in these patients associated with their reduced intestinal tract mucosal function. For example, GLP-2 or GLP-2 analog is administrated to a patient with an inflammatory bowel condition in an amount sufficient to ameliorate the intestinal discomfort and diarrhea caused by the condition. Additionally, GLP-2 or a GLP-2 analog may be administered to patients with malabsorption disorders so as to enhance the nutritional absorption and thereby improve the nutritional status of such patients.

In general, patients who would benefit from either increased small intestinal mass and consequent increased small bowel mucosal function are candidates for treatment with GLP-2 or GLP-2 analog. Particular conditions that may be treated with GLP-2 include the various forms of sprue including celiac sprue which results from a toxic reaction to α-gliadin from wheat, and is marked by a tremendous loss of villae of the bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the GLP-2 treatment may be monitored by enteric biopsy to examine the villus morphology, by biochemical assessment of nutrient absorption, by patient weight gain, or by amelioration of the symptoms associated with these conditions.

Other conditions that may be treated with GLP-2 or GLP-2 analog, or for which GLP-2 or GLP-2 analog may be useful prophylactically, include radiation enteritis, infectious or post-infectious enteritis, regional enteritis (Crohn's disease), small intestinal damage due to toxic or other chemotherapeutic agents, and patients with short bowel syndrome.

In another aspect, patient candidates for treatment with GLP-2 or GLP-2 analog are those who would benefit from growth of pancreatic islets, and particularly from enlargement or proliferation or regeneration of pancreatic islets. Such patients include those suffering from diseases or conditions marked by the absence or reduction of pancreatic islets or by reduced pancreatic islet function. Particular patient candidates are those suffering from type 1 or type 2 diabetes, as well as patients with secondary forms of diabetes due to infiltration, inflammation or destruction of the pancreas. GLP-2 or GLP-2 analog is administered to these patients in an amount sufficient to restore at least partial pancreatic function, increase the level of endogenous insulin, and ameliorate their symptoms.

The therapeutic dosing and regimen most appropriate for patient treatment will of course vary with the disease or condition to be treated, and according to the patient's weight and other parameters. The results presented hereinbelow demonstrate that a dose of GLP-2 or GLP-2 analog equivalent to about 2.5 mg/kg (or less, see below) administered twice daily over 10 days can generate very significant increases in small bowel mass and in crypt/villus height particularly of the proximal jejunum. It is expected that much smaller doses, e.g., in the $\mu$g/kg range, and shorter or longer duration or frequency of treatment, will also produce therapeutically useful results, i.e., a statistically significant increase particularly in small bowel mass. The dosage sizes and dosing regimen most appropriate for human use are guided by the results herein presented, and can be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Primary among these is the amount of GLP-2 normally circulating in the plasma, which is on the order of 151 pmol/mL in the resting state, rising to 225 pmol/mL after nutrient ingestion for healthy adult humans. Orskow, C. and Helst, J. J., 1987, Scand. J. Clin. Lav. Invest. 47:165. Additional factors include the size of the patient, the age of the patient, the general condition of the patient, the particular disease being treated, the severity of the disease, the presence of other drugs in the patient, the in vivo activity of the GLP-2 peptide and the like. The trial dosages would be chosen after consideration of the results of animal studies and the clinical literature. It will be appreciated by the person of ordinary skill in the art that information such as binding constants and Ki derived from in vitro GLP-2 binding competition assays may also be used in calculating dosages.

A typical human dose of a GLP-2 peptide would be from about 10 $\mu$g/kg body weight/day to about 10 mg/kg/day, preferably from about 50 $\mu$g/kg/day to about 5 mg/kg/day, and most preferably about 100 $\mu$g/kg/day to 1 mg/kg/day.

In another of its aspects, the invention provides for the treatment of patient candidates as just identified using implanted cells that have either been conditioned in vitro or in vivo by prior incubation or treatment with GLP-2 or GLP-2 analog, or have been engineered genetically to produce it. Conditioning of the cells ex vivo can be achieved simply by growing the cells or tissue to be transplanted in a medium that has been supplemented with a growth-promoting amount of the GLP-2 or GLP-2 analog and is otherwise appropriate for culturing of those cells. The cells can, after an appropriate conditioning period, then be implanted either directly into the patient or can be encapsulated using established cell encapsulation technology, and then implanted.

Yet another aspect of the invention encompasses treating animals in vivo with GLP-2 peptides in order to promote the growth of small bowel tissue or to increase pancreatic islet cell size or numbers. After subsequent enlargement of the small bowel and/or pancreatic islets, these tissues may then be used in a xenotransplantation procedure. Such GLP-2 peptide treatment can be advantageous prior to xenotransplantation of tissue from a non-human animal to a human because the size of the transplanted organ or tissue often limits the success of this procedure. For example, a porcine donor animal may be treated with GLP-2 peptide in order to increase small bowel size prior to xenotransplantation of the porcine small bowel tissue into a human in need of this organ.

Alternatively, the cells to be implanted can be raised in vitro from a cell that has been engineered genetically to express or to over-express either the glucagon gene or, more directly, DNA coding solely for GLP-2. The sequence of such DNA can readily be determined from the amino acid sequence of the selected GLP-2, with the limitation that only GLP-2 forms containing genetically encoded amino acids can be produced in this manner. Various viral vectors, suitable for introduction of genetic information into human cells, can be employed and will incorporate the GLP-2-encoding DNA under expression controls functional in the host cells. Once altered genetically, the engineered cells can then be implanted using procedures established in the art.

Example 1

In a first experiment designed to investigate the effect of glicentin on small bowel growth, two groups of six mice (8 week, CD1 females from Charles River Laboratories) were treated as follows. Each mouse received 41.5 $\mu$g injections every 12 hours for 10 days. The injections were delivered subcutaneously in a final volume of 16% gelatin, with 0.5 cc injected subcutaneously every 12 hours. The glicentin (rat) dissolved easily in 10 ml water. Control mice received 0.5 cc of 16% gelatin solution, but no peptide, every 12 hours. Mice were fed standard rat chow with free access to food and water, until 12 hours prior to sacrifice, at which time food was withheld, and water only was given. The weight of the small bowel was ascertained by excising the entire small bowel, and removing the stomach (proximal end) and appendix/cecum/large bowel (distal end). The remaining small bowel was cleaned with saline to remove feces, and weighed. Results were as follows:

|  | Weight of Mice (gm) | | Small bowel weight (gm) |
| --- | --- | --- | --- |
|  | Day 0 | Day 10 | Day 10 |
| Control | 30.0 | 27.8 | 1.6 |
|  | 29.8 | 27.5 | 1.3 |
|  | 28.7 | 25.6 | 1.7 |
|  | 28.8 | 25.8 | 1.2 |
|  | 28.0 | 25.8 | 0.7 |

13

-continued

| | Weight of Mice (gm) | | Small bowel weight (gm) |
|---|---|---|---|
| | Day 0 | Day 10 | Day 10 |
| Glicentin | 27.9 | 26.2 | 1.3 |
| | 27.9 | 26.6 | 1.6 |
| | 27.1 | 26.2 | 1.7 |
| | 28.0 | 26.6 | 1.3 |
| | 24.8 | 24.5 | 1.6 |
| | 27.2 | 24.7 | 1.7 |
| | 26.5 | 25.8 | 1.9 |

With these results indicating that the intestinotrophic effect of glicentin was modest, a second experiment using the same protocols was performed to investigate the effects of other proglucagon gene-derived products, including GLP-1 and GLP-2. For this purpose, rat GLP-2 of SEQ ID NO:3 and human GLP-1 (7–36 amide) were custom synthesized by application of the tBoc-based solid phase approach. Analysis of the rat GLP-2 revealed a purity of 95% by analytical HPLC (20 μl sample of 1.0 mg/ml; 5 μ Vydac C18 column; 0.1% TFA/20–60% CH$_3$CN over 20 mins at 1.5 ml/min).

GLP-2 formulations for injection were prepared as follows: Gelatin was dissolved in warm water to a weight ratio of 16%, and the 50 mL solution was autoclaved and cooled to room temperature. A peptide solution was then separately prepared by mixing 5 mg of GLP-2 with water at a volume slightly less than 10 mL, and then adding 1N acetic acid in a volume (10–20 μL) sufficient to dissolve the peptide completely. The pH was then readjusted to about 7.0 by addition of an equal volume of 1N NaOH (10–20 μL), and the solution volume was then adjusted to 10 mL by addition of distilled water. To prepare the formulation for injection, the 10 mL peptide solution and the 50 mL solution of 16% gelatin were combined with mixing, and aliquots for injection were drawn into a 0.5 mL insulin syringe. The same procedure was used to formulate the GLP-1, with the exception that no acid/base adjustment was necessary given its relative greater solubility in water.

Mice were injected with 0.5 ml of the 16% gelatin solution, without or with peptide (62.5 μg/dose). Four groups of four mice (8 week, CD1 females from Charles River Laboratories) were injected twice daily for 10 days. Results are tabulated below:

| | Weight of Mice (gm) | | Small bowel weight (gm) | | |
|---|---|---|---|---|---|
| | Day 0 | Day 10 | Day 10 | Average | % body wt |
| Control | 26.0 | 25.4 | 1.4 | 1.4 ± .04 | 5.47 ± .14 |
| | 27.0 | 25.9 | 1.3 | | |
| | 26.0 | 26.7 | 1.5 | | |
| | 25.6 | 24.4 | 1.4 | | |
| GLP-1 | 26.6 | 24.8 | 1.4 | 1.33 ± .04 | 5.26 ± .2 |
| | 23.2 | 22.8 | 1.3 | | |
| | 26.0 | 27.0 | 1.2 | | |
| | 25.1 | 26.5 | 1.4 | | |
| GLP-2 | 25.2 | 23.7 | 1.8 | 2.08 ± .14 | 8.12 ± .40 |
| | 27.1 | 25.7 | 2.3 | | |
| | 28.4 | 27.1 | 2.4 | | |
| | 25.8 | 25.4 | 1.8 | | |

These results demonstrate that, at a dose of about 2.5 mg/kg (640 nmole/kg), GLP-2 exhibits a statistically significant (p<0.05) increase in the mass of small bowel after twice daily treatment for 10 days, relative both to the control group receiving no peptide, and to the group receiving

14 another glucagon-related peptide, GLP-1. Relative to the results presented here for glicentin, it is also clear that GLP-2 constitutes a major intestinal tissue growth factor.

Effects of the administration of GLP-2 peptide to these mice was further explored, by sectioning gastrointestinal organs of the four GLP-2 treated mice and the four control mice, using paraffin embedded sections and standard histopathological techniques. Islet areas were measured by morphometric analysis. Hematoxylin and eosin-stained sections were used for quantification. Total pancreatic area and total islet area in each section were measured. The data revealed that islet area was, on average, 0.31% of the total pancreatic area in the control group. On the other hand, islets of the GLP-2-treated group constituted 0.76% of total pancreatic area, representing an increase in islet area of more than double in the GLP-2-treated group. In addition to islet size, an increase in the number of islets was observed.

Example 2

The effects of GLP-2 peptide on the growth of small bowel were further investigated, particularly to assess tissue response as a function of dose, time, administration route and frequency, formulation type, and gender and age of recipient. These effects were measured in the context not only of increased small bowel mass, but also in the context of increased crypt and villus height.

To these ends, rat GLP-2 was prepared as described in Example 3. The rat GLP-2 was formulated either in phosphate buffered saline or as a gelatin-containing depot formulation. To prepare the phosphate buffered saline solution, the GLP-2 peptide was prepared as follows: A 10X stock PBS solution was first prepared, using 80 g NaCl (BDH ACS 783), 2 g KCl (BDH ACS 645), 11.5 g Na$_2$HPO$_4$ (Anachemia AC-8460), and 2 g KH$_2$PO$_4$ (Malinckrodt AR7100), which was brought to a total volume of one liter with sterile distilled water. The final working solution was obtained by 10:1 dilution of the stock solution with sterile distilled water and adjusted to pH 7.3–7.4 if necessary using several microliters of 10N NaOH (sodium hydroxide). The working solution was then autoclaved for 30 minutes. In the final working PBS solution, concentrations were 137 mM NaCl, 2.7 mM KCl, 4.3 mM Na$_2$HPO$_4$.7H$_2$O, and 1.4 mM KH$_2$PO$_4$.

To generate the PBS-formulated GLP-2 peptide, the powdered peptide was added to the working PBS solution as required to formulations having the desired peptide concentrations. For example, to generate a PBS solution of peptide at 130 mg/L, 4.2 mg of GLP-2 were dissolved in 40 ml PBS to yield a GLP-2 concentration of 130 ug/ml. To deliver a dose at 2.5 mg/kg to a mouse, approximately 0.5 ml of this solution would be injected twice a day.

To generate the gelatin-based formulation, a gelatin solution was first prepared by dissolving 12 grams of gelatin (Sigma, G-8150 Lot #54H07241 Type A from Porcine skin [9000-70-8] ~300 Bloom) in 100 mL distilled water. The gelatin solution was then autoclaved, warmed at 37° C., and the GLP-2 peptide previously dissolved in phosphate buffered saline as described above was added to achieve specific, desired peptide concentrations. Gelatin-based GLP-2 formulations were then prepared at the desired GLP-2 concentration by mixing the PBS-formulated GLP-2 with the gelatin solution prepared as just described. For instance, to generate a gelatin-based PBS solution of the GLP-2 at a concentration of 130 mg/L, 10 ml of a PBS solution prepared with 4.2 milligrams GLP-2 was diluted with 30 ml of the 20% working gelatin solution prepared as described above. The solution was mixed by gentle pipetting, to yield a final solution of 130 mg/L GLP-2 in PBS with 15% gelatin.

As in Example 1, recipients were CD1 mice obtained from Charles River Laboratory (Ontario, Canada). The CD1 mice were aged-matched females at time of injection (n=3–4 per group), 6 weeks of age, unless otherwise specified. The animals were allowed a minimum of 24 hours to acclimatize to the laboratory facility before the initiation of each experiment. Animals were identified by ear punch. The mice were not restricted by diet or activity during the experiments. The light/dark cycle was 12 hours, between 6 pm to 6 am. The majority of the injections used 12% gelatin or PBS as vehicle. Controls were age- and sex-matched (n=3–4) animals that were injected with PBS or gelatin formulation. Each peptide was prepared at a specific concentration, dissolved in 0.5 cc of vehicle. The peptides were injected subcutaneously and mice were monitored daily in the laboratory facility. Animals were sacrificed 14 days after injection, and were fasted 20–24 hours before sacrifice.

The mice were anaesthetised with $CO_2$ and exsanguinated by cardiac puncture. Blood was collected in 75 $\mu$l of TED (Trasysol; EDTA (5000 KIU/ml: 1.2 mg/ml; Diprotin-A), and the blood was centrifuged at 14 k×g for 5 minutes and the plasma was stored at −70 prior to analysis. The small bowel was removed from the peritoneal cavity, from pylorus to cecum, cleaned weighed and measured. For comparative purpose, sections from each animal were obtained from the identical anatomical position. Fragments each measuring 1.5–2.0 cm in length were obtained 8±2 cm, 18±2 cm, 32±2 cm from pylorus for histomorphometry representing proximal jejunum, distal jejunum and distal ileum. Each small bowel fragment was opened longitudinally on its antimesenteric border in a tissue block and then placed on 10% formalin (vol./vol.) overnight, then transferred to 70% ETOH.

For micrometry and morphometric analysis, and particularly to assess GLP-2 effects on crypt/villus height, 5 $\mu$m thick sections were cut and stained with hematoxylin and eosin. Intestinal micrometry was performed using a microscope with a video camera (Leitz, Wetzar, Germany.) connected to a computer monitor. The microscope was calibrated at 4x, 10x, 25x magnification and the same microscope was used for all evaluations. Crypt plus villus height was measured by examining at least 20 longitudinally-oriented villi from the base of the crypt to the tip of the villus from each slide for proximal and distal jejunum and distal ileum and is expressed in $\mu$m+S.E.M.

Results of the various analyses are shown in the accompanying FIGS. 1–7 and 9, and are summarized below with reference to those Figures:

Dose Response: FIG. 1 illustrates the response to rat GLP-2 measured as small bowel weight (BW - panel A) and as crypt plus villus height in proximal jejunum (PJ-panel B), distal jejunum (DJ-panel C) and distal ileum (DI-panel D) as a function of rat GLP-2 dose in a 12% gelatin formulation (i.e., GLP-2 in PBS) administered s.c. The rat GLP-2 peptide was administered subcutaneously. Results are expressed as percent change of control receiving 12% gelatin as vehicle only. Asterisks denote statistically significant differences compared to control (*=p<0.005, =p<0.01, *=p<0.001). It will be appreciated from the results presented in FIG. 1 that the injection of GLP-2 peptide results in statistically significant increases in small bowel weight at a dose of 1.0 to 5.0 $\mu$g. The desired effect on crypt/villus height is realized at doses as low as 0.25 $\mu$g.

Effect of Formulation: FIG. 2 illustrates results obtained using the gelatin-based formulation (G) or the PBS formulation (PBS), when administered s.c. at a GLP-2 dose of 2.5 $\mu$g twice a day. Panel A illustrates differences in effect seen in small bowel weight in grams, and panel B illustrates differences in effect seen on crypt/villus height in $\mu$m seen for proximal (PJ) and distal (DJ) jejunum and distal ileum (DI). It will be appreciated that both formulation types elicited a statistically significant increase. Presumably because of its ability to release the GLP-2 in a more sustained manner from the injection site, the gelatin-based formulation elicited a slightly greater response than did the PBS formulation.

Figure 3:
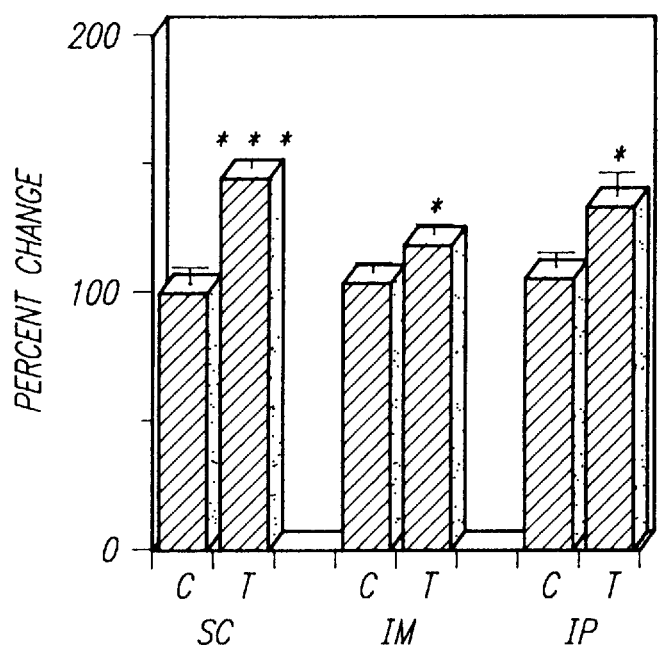

Effect of Administration Route: FIG. 3 illustrates the percentage increase in bowel weight (BW) when rat GLP-2, at a dose of 2.5 $\mu$g twice a day, is injected either subcutaneously (SC), intramuscularly (IM) or intraperitoneally (IP) in the phosphate-buffered saline vehicle. It will be appreciated that a significant response to the GLP-2 peptide was elicited regardless of the selected administration route, relative to a control group receiving s.c. administration of PBS vehicle alone. Sub-cutaneous injection provided the greatest response.

Figure 4:
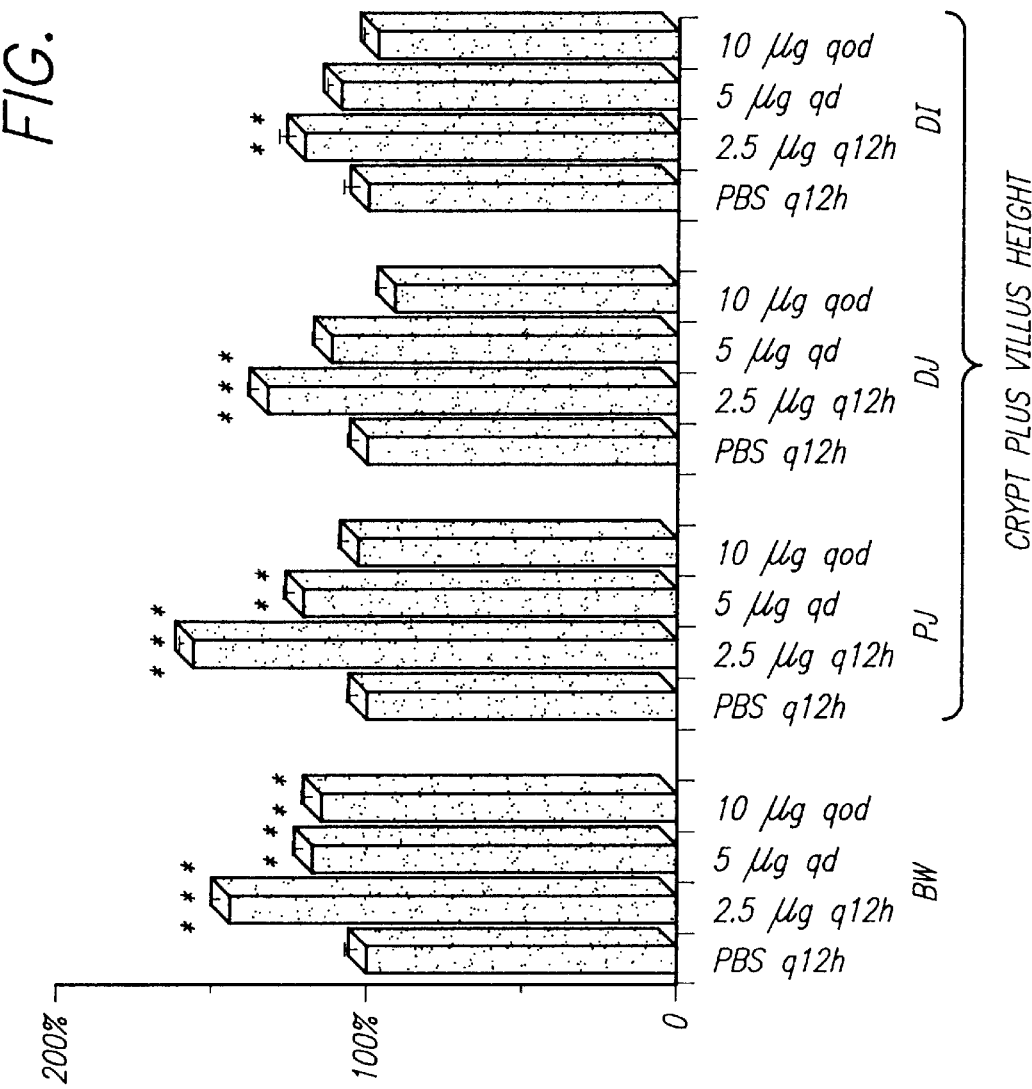

Effect of Administration Frequency: FIG. 4 illustrates results from an assessment of small bowel weight and crypt/villus height as a function of the frequency of GLP-2 administration. The GLP-2 was administered s.c. at the noted dose, either every twelve hours (q12 h), once a day (qd) or once every other day (qod). It will be appreciated from the results illustrated that all frequencies of administration elicited an increase of significance in the percent change of small bowel weight, relative to a control group receiving PBS alone. The greatest increase was elicited, for small bowel weight and for crypt/villus height, by the most frequent dosing schedule, i.e., every 12 hours.

Figure 5A:
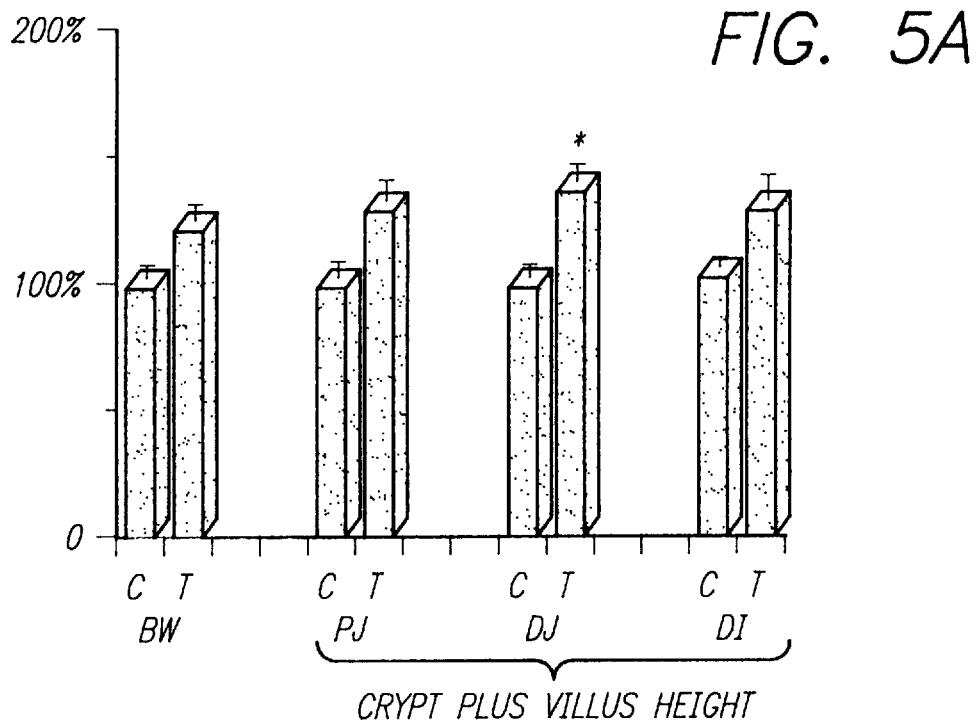
Figure 5B:
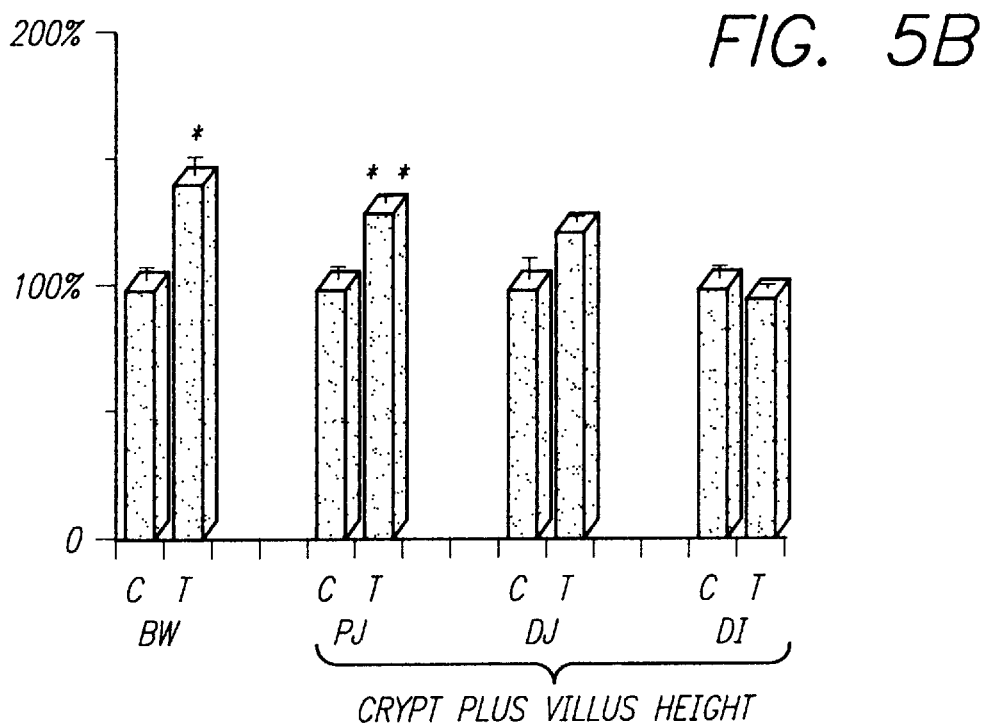
Figure 5C:
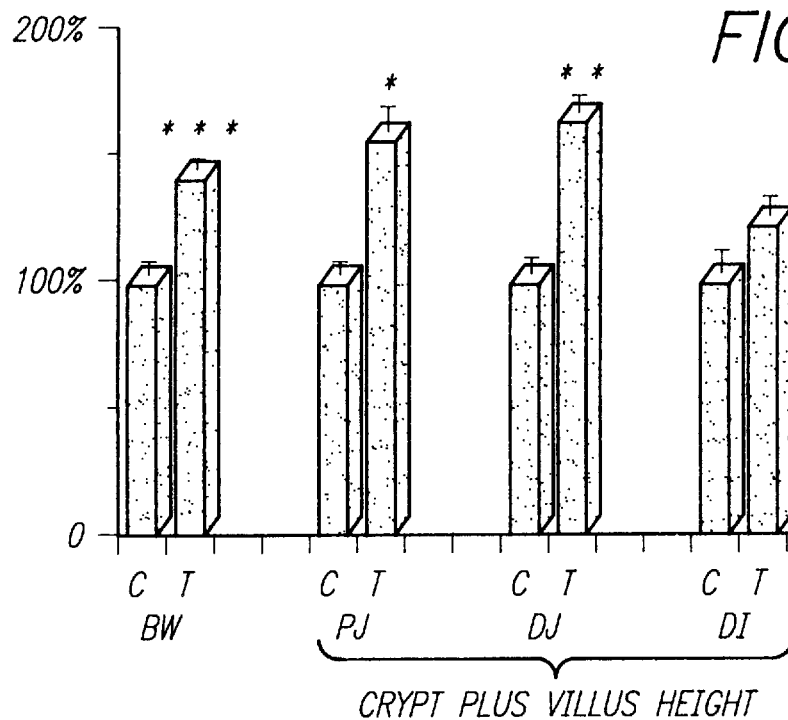

Effect of Long Term Administration: Rat GLP-2 in a 10% gelatin formulation was administered s.c. in a single dose of 5 $\mu$g once a day continuously for 4 weeks (panel A), for 8 weeks (panel B) or for 12 weeks (panel C). FIG. 5 illustrates GLP-2 mediated effects on small bowel weight (BW) and in the crypt plus villus heights (PJ, DJ and DI) in treated groups (T), relative to a control (C) receiving 10% gelatin alone. Results for small bowel weight indicate that the GLP-2 mediated small bowel weight increase is induced and sustained over the examined term of administration, as does the crypt/villus height of the proximal jejunum. A similar response was noted also for the distal jejunum. All animals received a complete autopsy at the time of sacrifice and there were no histological abnormalities found in any of the animals.

Figure 6:
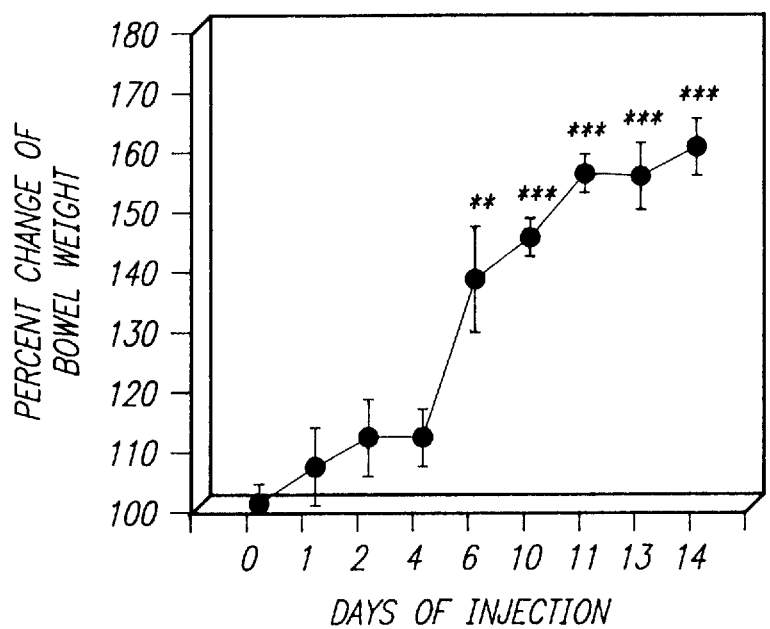
Figure 7A:
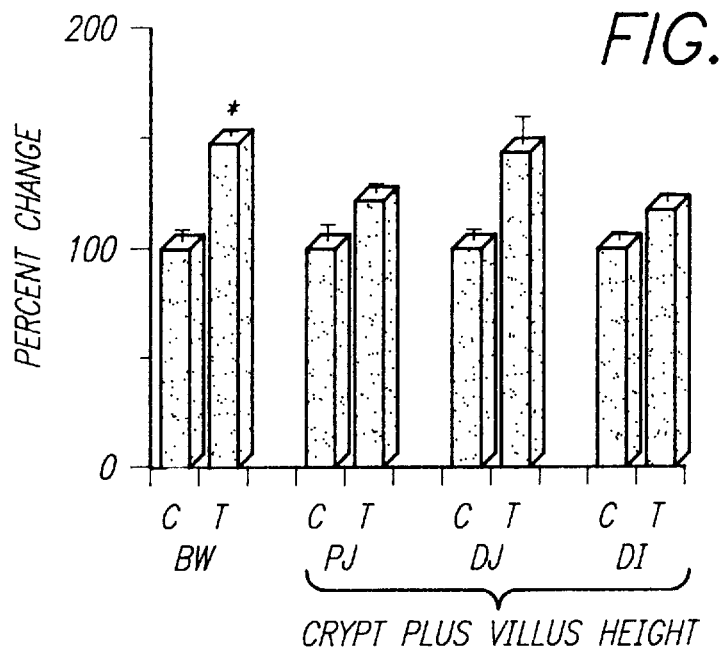
Figure 7B:
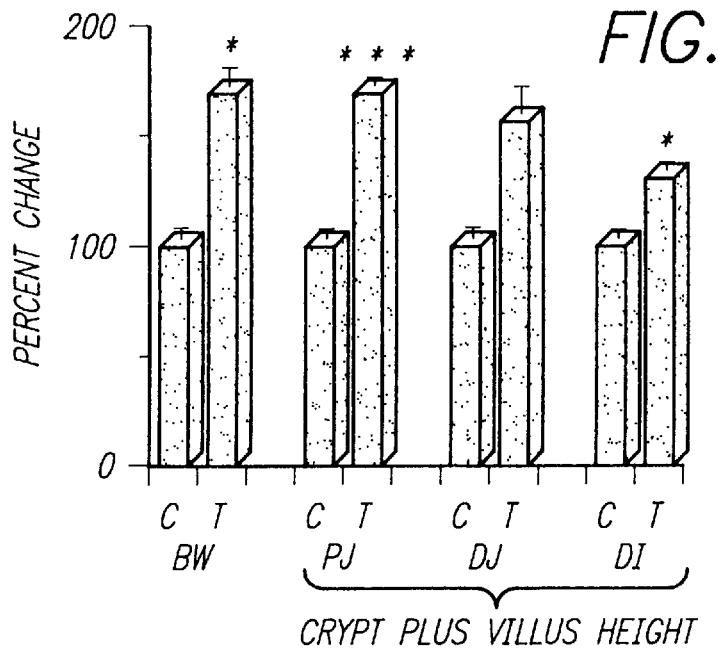
Figure 7C:
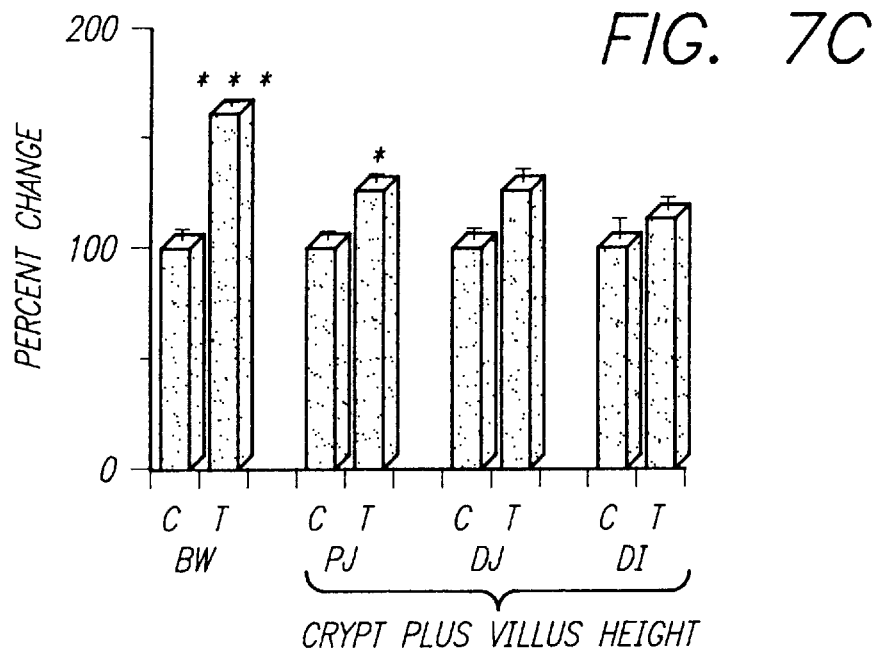
Figure 7D:
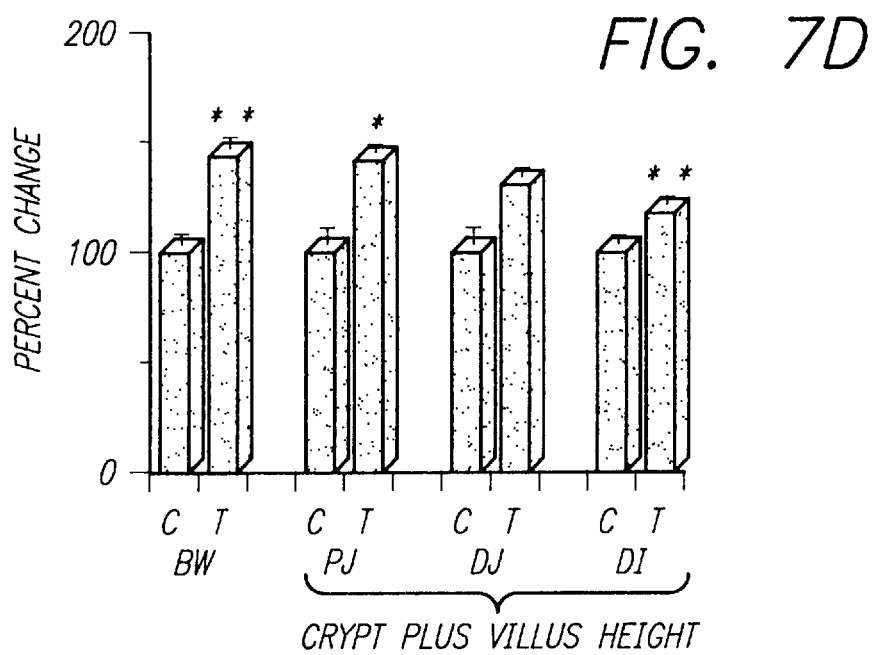
Figure 7E:
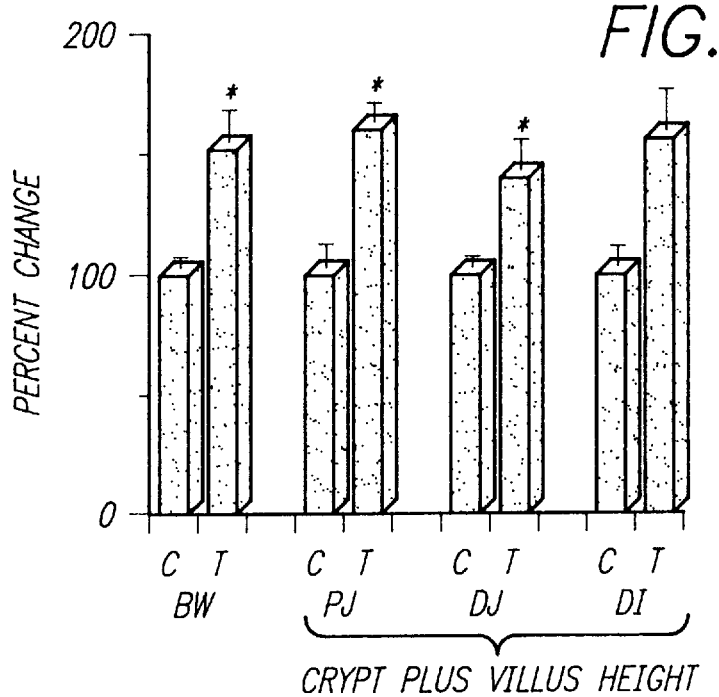
Figure 7F:
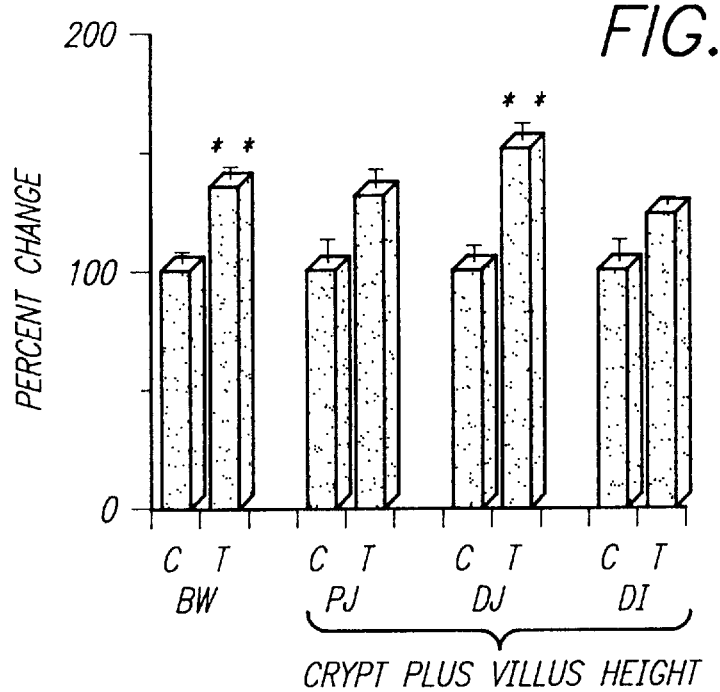
Figure 7G:
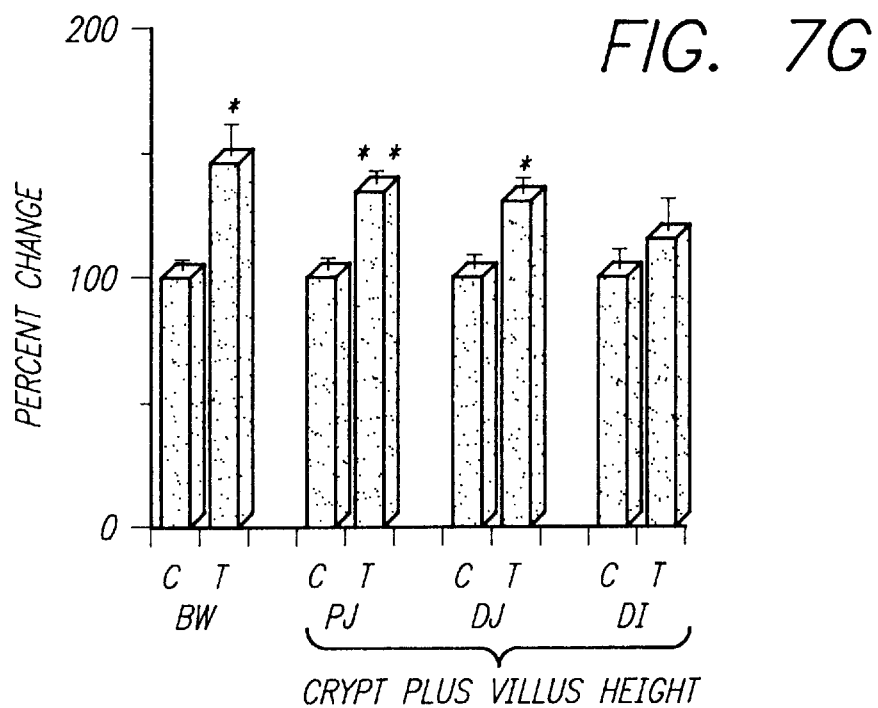
Figure 7H:
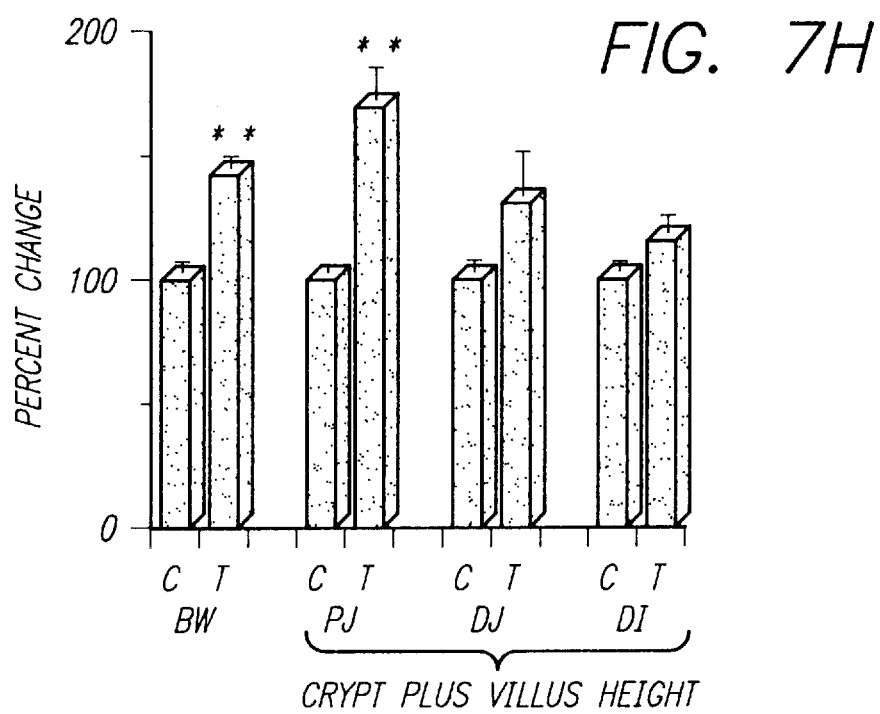

Time Course Assessment: FIG. 6 presents the percentage change in small bowel weight measured in female CD-1 mice treated subcutaneously with PBS alone (Control) or with 2.5 $\mu$g rat GLP-2 in PBS administered twice daily for the noted number of consecutive days. It is clear from the results that a significant result is attained after the 4th day of administration, and that this effect is sustained with continuing administration. In other studies, it is clear also that the increased small bowel weight attained with administration of GLP-2 has regressed about 10 days post-treatment. However, the GLP-2 effects on the villus hyperplasia did not completely regress, particularly in the older (24 month old) mice which suggests a slower rate of intestinal tissue turnover in these older recipients. It is thus appropriate to place recipients on a maintenance dosing regimen during GLP-2 therapy.

Recipient Gender and Age Assessment: FIG. 7 illustrates results obtained with sex-matched CD-1 mice treated with 2.5 $\mu$g of GLP-2 twice daily from 4 to 16 weeks of age, compared to their own controls for both small bowel weight and histology. It will be appreciated from the results presented that GLP-2 effects on small bowel are elicited independently of the recipient's gender. In a related experiment, female C57BLK mice (Charles River, U.S.) aged 6 months to 2 years treated with GLP-2 were assessed and GLP-2 was found to be effective in promoting small bowel growth in mice from 6 months to 2 years of age.

Figure 9:
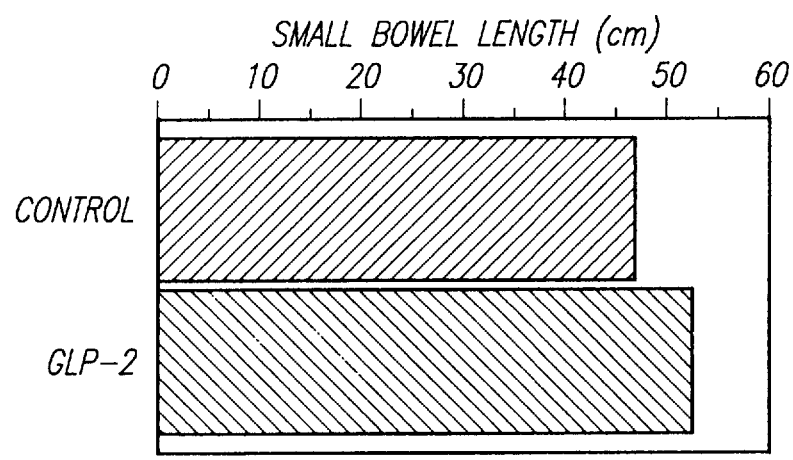

Assessment of GLP-2 Effects on Small Bowel Length: FIG. 9 illustrates the effect of GLP-2 administration on small bowel length. CD1 mice were treated with PBS (Control) or rat GLP-2 (2.5 μg twice daily) in PBS for 10 days, following which mice were sacrificed and the small bowel length from stomach to ileocecal valve was measured in centimeters.

The villus elongation observed in response to GLP-2 may arise either from a GLP-2 effect on cell proliferation or on inhibition of senescence. To examine these two possibilities, paraffin sections of small bowel from stimulated and control tissues were examined to detect proliferating cell nuclear antigen (PCNA), as a measure of proliferation, and to detect apoptotic cells using the TUNEL method for apoptosis analysis. Proliferation rates in the proximal jejunum of GLP-2-treated mice were increased (124%) over control mice (46.0±1.2% in control; 57±5.5% in treated). In control mice, proliferation was confined to the crypt compartment of the small bowel; the villi did not contain PCNA-positive cells. In the GLP-2-treated group, proliferating cells were detected in the villi, and at the junction of the crypt-villus axis. Apoptotic rates in the proximal jejunum of GLP-2-treated mice were decreased over control mice. Apoptotic cells in control mice were found mainly on the tip or edge of the villi; none were found in the crypt compartment of the intestine. In the GLP-2 treated mice, distribution of apoptotic cells was similar, but their numbers were fewer.

Example 3

Given the results observed with rat GLP-2 in mice recipients, it was surmised that various vertebrate homologs and analogs of rat GLP-2 would also mediate an intestinotrophic effect. To this end, a variety of GLP-2's and GLP-2 analogs were synthesized and assessed, as described below.

Solid phase peptide synthesis (SPPS) was carried out manually in a 300 milliliter (mL) vessel on a 3 millimole (mmole) scale using 6 grams (g) of chloromethyl (Merrifield) resin (for C terminal free acid peptides) with a substitution of 0.5 milliequivalents (meq) per gram. Amino acids were protected at the amino-terminus with the t-butyloxycarbonyl (tBoc) group. The side chains of the amino acids were protected with the benzyl (Bz, for serine and threonine), benzyloxymethyl (BOM, for histidine), 2-bromobenzyloxycarbonyl (2-BrZ, for tyrosine), 2-chlorobenzyloxycarbonyl (2-ClZ, for lysine), cyclohexyl (cHex, for aspartic and glutamic acids), and tosyl (Ts, for arginine) side-chain protecting groups, and chloromethyl (Merrifield) resin. The first amino acid was coupled to the chloromethyl resin through esterification of the protected amino acid in the presence of potassium fluoride (KF). C-terminal amide peptides were synthesized on a 4-methylbenxhydrylamine (MBHA) resin on a 3 mmol scale using 6 g of resin with a substitution of 0.5 milliequivalents/g. The first amino acid was coupled to the MBHA resin according to the procedure described for peptide elongation.

Amino-group deprotection was carried out using 50% trifluoroacetic acid (TFA) in $CH_2Cl_2$, followed by neutralization using two washes of 10% triethylamine ($Et_3N$) in $CH_2Cl_2$. Peptide elongation was carried out using N,N-dicyclohexylcarbodiimide/1-hydroxybenzotriazole (DCC/HOBt) in $CH_2Cl_2$/dimethylformamide (DMF). The growing peptide chain was capped after each elongation step with 20% acetic anhydride ($Ac_2O$) in dichloromethane ($CH_2Cl_2$). The peptide-resin was washed after each elongation, capping and deprotection step with isopropanol (iPrOH) and methanol (MeOH). The washes were repeated once. N-terminal acetyl peptides were prepared by acetylation of the terminal amino-group with 20% $Ac_2O$ in $CH_2Cl_2$. Resin-bound products were routinely cleaved by a low-high procedure using hydrogen fluoride (HF) containing dimethylsulfide (DMS) and p-cresol as scavengers.

Crude peptides were purified by preparative high pressure liquid chromatography (HPLC) using a Vydac C18, 15–20 μm wide pore, 2 inch×12 inch, reverse phase silica column using gradient elution with 0.1% TFA in water modified with acetonitrile. Elution was monitored at 220 nanometers (nm). Each fraction collected was analyzed for purity by analytical HPLC using a Vydac C18, 5 μm, 4.6×254 millimeter(mm), reverse-phase silica column by gradient elution with 0.1% TFA in water modified with acetonitrile, and monitored at 215 nm. Fractions demonstrating greater than 95% purity were combined and lyophilized. Acetate salts of the peptides were prepared from the TFA salts by dissolution of the lyophilized powder in water, with addition of acetonitrile to aid in dissolution where necessary. The solution was passed through a protonated Bio-Rex 70 cation exchange resin. The resin was washed with 5 bed-volumes of water, and the resin-bound peptide eluted with 50% acetic acid in water. The eluent was diluted with water and lyophilized.

The final lyophilized powder was analyzed for purity by two analytical reverse-phase HPLC methods using a Vydac C18, 5 μm column, 4.6×254 mm reverse-phase silica column. The two solvent systems used were a gradient of water adjusted to pH 2.25 with triethylamine phosphate, modified with acetonitrile, and a gradient of 0.1% TFA in water, modified with acetonitrile. The column eluent was monitored at 215 nm. The identity of each product was confirmed by amino acid analysis and by electrospray mass spectrometry..

By this method, there were produced the following GLP-2 or GLP-2 analogs, as acetates:
a) rat GLP-2 of SEQ ID NO;3;
b) N-acetyl rat GLP-2, in which the amino terminus of rat GLP-2 was blocked with an acetyl group;
c) [$Arg^{+1}$] rat GLP-2, which is rat GLP-2 modified by an additional Arg residue to the amino terminus;
d) C-amido rat GLP-2, which is rat GLP-2 with an amido group added to the carboxyl terminus (dissolution of 1 mg was achieved in 1% acetic acid (110 μl), neutralized with 450 μl 5N NaOH);
e) [$Arg^{+1,+2}$] rat GLP-2, which is rat GLP-2 modified by two additional Arg residues present at the amino terminus;
f) [Arg+34] human GLP-2, which is human GLP-2 with an Arg residue added after residue 33; and
g) degu GLP-2.
These peptides were fully soluble in water at room temperature unless otherwise noted.

The intestinotrophic effect of these GLP-2's and GLP-2 analogs was assessed in the manner described in Example 2. In particular, peptides were formulated in PBS at a dose of 2.5 μg per 0.5 ml injection, and administered subcutaneously to female CD-1 mice every 12 hours for 10 or 14 days. Bowel weight and crypt villus height were compared against mock-treated mice (PBS alone).

Figure 8G:
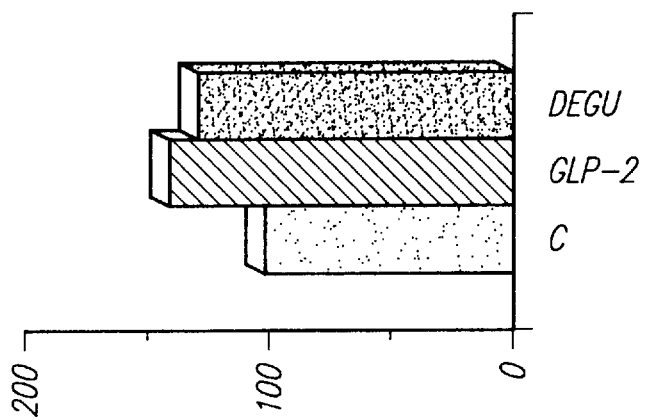
Figure 8F:
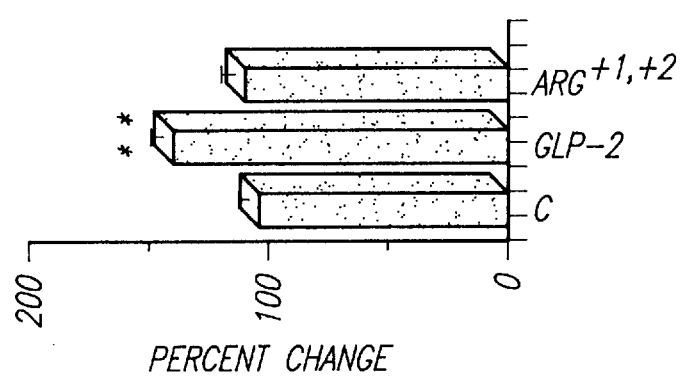
Figure 8E:
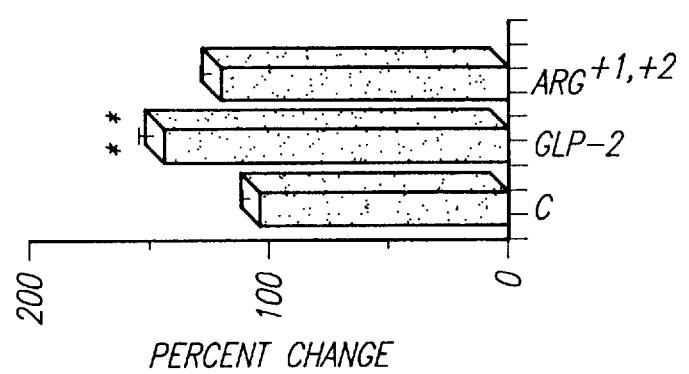

The results of these experiments are presented in FIG. 8. The peptides which were modified from GLP-2 by addition of chemical groups to the amino terminus, specifically [N-acetyl]-GLP-2, or contained additional amino acid(s) to the N-terminus, [Arg$^{+1}$]-GLP-2, or to the carboxyl terminus, such as [Arg$^{+34}$]-GLP-2, resulted in GLP-2 derivatives that still exhibited small bowel growth factor properties in vivo, as exemplified by their efficacy in promoting small bowel growth and increased crypt plus villus height (compared to saline-treated controls) in a 14-day experiment in mice (FIG. 8, panels A–F). Furthermore, GLP-2-related molecules with effective small bowel growth factor-like properties may be prepared by utilizing information derived from the sequences of related GLP-2-like molecules from various species. For example, the degu GLP-2 sequence also demonstrates small bowel growth factor-like activity in a 10-day experiment in mice, with an increase in small bowel weight nearly comparable to that achieved with rat GLP-2 (both peptides administered subcutaneously at 2.5 $\mu$g twice a day). This data demonstrates that these modifications of the GLP-2 peptide structure, as illustrated here, result in molecules that exhibit native GLP-2-like properties in vivo. In contrast, when the carboxyl terminal region of the molecule was modified by addition of a amino blocking group, [C-amido]-GLP-2, the resulting peptide did not exhibit significant GLP-2 biological activity in vivo (FIGS. 8C–D).

EQUIVALENTS

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

---

What is claimed is:

1. A pharmaceutical composition, comprising a GLP-2, or a pharmaceutically acceptable salt thereof, and a pharmaceutically acceptable carrier, which has the formula (SEQ ID NO. 1):

R1-(Y)m-His-Ala-Asp-Gly-Ser-Phe-Ser-Asp-Glu-Met-Asn-Thr-aa1-Leu-Asp-aa2-Leu-Ala-aa3-aa4-Asp-Phe-Ile-Asn-Trp-Leu-aa5-aa6-Thr-Lys-Ile-Thr-Asp-(X)n-R2 wherein:
aa1 is Met, Leu, Ile, Val or Cys;
aa2 is Ala, Ser, Thr, Pro, Gly, Asn, Asp, Glu or Gln;
aa3 is Ala, Ser, Thr, Pro or Gly;
aa4 is His, Arg or Lys;
aa5 is Met, Leu, Ile, Val or Cys;
aa6 is Asn, Asp, Glu, Gln, His, Arg or Lys;
X is one or two amino acids selected from the group consisting of His, Arg and Lys;
Y is one or two amino acids selected from the group consisting of His, Arg and Lys;
m is 0 or 1;
n is 0 or 1;
R1 is H or an N-terminal blocking group; and
R2 is OH or a C-terminal blocking group, and wherein the GLP-2 or salt thereof is not a naturally occurring GLP-2.

2. The pharmaceutical composition according to claim 1, wherein the GLP-2 or salt thereof is present in an amount effective to promote the growth of gastrointestinal tissue.

3. A method for promoting the growth of bowel tissue in a patient in need thereof, comprising administering to the patient an effective amount of a pharmaceutical composition as claimed in claim 1 to promote the growth of bowel tissue.

4. The pharmaceutical composition according to claim 1, wherein the GLP-2 or salt thereof is present in an amount effective to promote the growth of pancreatic islets.

5. A method for promoting the growth of pancreatic islets in a patient in need thereof, comprising administering to the patient an effective amount of a pharmaceutical composition as claimed in claim 1 to promote the growth of pancreatic islets.

6. A method for treating a gastrointestinal disease selected from the group consisting of ulcers, digestion disorders, malabsorption syndromes, short-gut syndrome, cul-de-sac syndrome, inflammatory bowel disease, celiac sprue, tropical sprue, hypogammaglobulinemic sprue, enteritis, regional enteritis (Crohn's disease), small intestinal damage due to toxic or chemotherapeutic agents, and short bowel syndrome, and wherein the method comprises administering to a patient having the gastrointestinal disease an effective amount of a pharmaceutical composition as claimed in claim 1 to reduce a pathological effect or symptom of the gastrointestinal disease.

7. A method for treating diabetes, comprising administering to a patient having diabetes an effective amount a pharmaceutical composition as claimed in claim 1 to increase the levels of insulin in the patient.

8. The pharmaceutical composition according to claim 1, wherein the GLP-2 or salt thereof has the amino acid sequence (SEQ ID NO. 2):

R1-(Y)m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-(X)n-R2.

9. The pharmaceutical composition according to claim 8, wherein the GLP-2 or salt thereof is present in an amount effective to promote the growth of gastrointestinal tissue.

10. A method for promoting the growth of bowel tissue in a patient in need thereof, comprising administering to the patient an effective amount of a pharmaceutical composition as claimed in claim 8 to promote the growth of bowel tissue.

11. The pharmaceutical composition according to claim 8, wherein the GLP-2 or salt thereof is present in an amount effective to promote the growth of pancreatic islets.

12. A method for promoting the growth of pancreatic islets in a patient in need thereof, comprising administering to the patient an effective amount of a pharmaceutical composition as claimed in claim 8 to promote the growth of pancreatic islets.

13. A method for treating a gastrointestinal disease selected from the group consisting of ulcers, digestion disorders, malabsorption syndromes, short-gut syndrome, cul-de-sac syndrome, inflammatory bowel disease, celiac sprue, tropical sprue, hypogammaglobulinemic sprue, enteritis, regional enteritis (Crohn's disease), small intestinal damage due to toxic or chemotherapeutic agents, and short bowel syndrome, and wherein the method comprises administering to a patient having the gastrointestinal disease an effective amount of a pharmaceutical composition as claimed in claim 8 to reduce a pathological effect or symptom of the gastrointestinal disease.

14. A method for treating diabetes, comprising administering to a patient having diabetes an effective amount of a pharmaceutical composition as claimed in claim 8 to increase the levels of insulin in the patient.

15. A method according to any of claims 3, 5, 6, 7, 10 or 12–14, wherein the patient is a human.

16. A method to identify intestinotrophic peptides, comprising:
   a) obtaining an analog of an intestinotrophic vertebrate GLP-2, the analog having at least one amino acid substitution, deletion, addition, or an amino acid with a blocking group;
   b) administering to a mammal the analog using a regimen capable of eliciting an intestinotrophic effect when utilized for rat GLP-2; and
   c) determining the effect of the analog on small bowel weight and/or on the crypt plus villus height and/or pancreatic islet size relative to a mock treated control mammal, whereby the intestinotrophic peptide is identified as an analog which elicits an increase in the weight and/or the height and/or the size.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "An amino acid selected from His, Arg, or Lys. Xaa may or may not be present in the sequence."

( i x ) FEATURE:
        ( A ) NAME/KEY: Modified-site
        ( B ) LOCATION: 2
        ( D ) OTHER INFORMATION: /note= "An amino acid selected from His, Arg, or Lys. Xaa may or may not be present in the sequence."

( i x ) FEATURE:
        ( A ) NAME/KEY: Modified-site
        ( B ) LOCATION: 15
        ( D ) OTHER INFORMATION: /note= "An amino acid selected from Met, Leu, Ile, Val or Cys."

( i x ) FEATURE:
        ( A ) NAME/KEY: Modified-site
        ( B ) LOCATION: 18
        ( D ) OTHER INFORMATION: /note= "An amino acid selected from Ala, Ser, Thr, Pro, Gly, Asn, Asp, Glu or Gln."

( i x ) FEATURE:
        ( A ) NAME/KEY: Modified-site
        ( B ) LOCATION: 21
        ( D ) OTHER INFORMATION: /note= "An amino acid selected from Ala, Ser, Thr, Pro or Gly."

( i x ) FEATURE:
        ( A ) NAME/KEY: Modified-site
        ( B ) LOCATION: 22
        ( D ) OTHER INFORMATION: /note= "An amino acid selected from His, Arg or Lys."

( i x ) FEATURE:

(A) NAME/KEY: Modified-site
(B) LOCATION: 29
(D) OTHER INFORMATION: /note= "An amino acid selected from Met, Leu, Ile, Val or Cys."

(ix) FEATURE:
(A) NAME/KEY: Modified-site
(B) LOCATION: 30
(D) OTHER INFORMATION: /note= "An amino acid selected from Asn, Asp, Glu, Gln, His, Arg or Lys."

(ix) FEATURE:
(A) NAME/KEY: Modified-site
(B) LOCATION: 36
(D) OTHER INFORMATION: /note= "An amino acid selected from His, Arg or Lys. Xaa may or may not be present in the sequence."

(ix) FEATURE:
(A) NAME/KEY: Modified-site
(B) LOCATION: 37
(D) OTHER INFORMATION: /note= "An amino acid selected from His, Arg or Lys. Xaa may or may not be present in the sequence."

(xi) SEQUENCE DESCRIPTION: SEQ ID NO:1:

```
Xaa Xaa His Ala Asp Gly Ser Phe Ser Asp Glu Met Asn Thr Xaa Leu
 1           5                   10                      15
Asp Xaa Leu Ala Xaa Xaa Asp Phe Ile Asn Trp Leu Xaa Xaa Thr Lys
         20              25                      30
Ile Thr Asp Xaa Xaa
         35
```

(2) INFORMATION FOR SEQ ID NO:2:

(i) SEQUENCE CHARACTERISTICS:
(A) LENGTH: 37 amino acids
(B) TYPE: amino acid
(C) STRANDEDNESS:
(D) TOPOLOGY: unknown (ii) MOLECULE TYPE: peptide (ix) FEATURE:
(A) NAME/KEY: Modified-site
(B) LOCATION: 1
(D) OTHER INFORMATION: /note= "An amino acid selected from His, Arg, or Lys. Xaa may or may not be present in the sequence."

(ix) FEATURE:
(A) NAME/KEY: Modified-site
(B) LOCATION: 2
(D) OTHER INFORMATION: /note= "An amino acid selected from His, Arg, or Lys. Xaa may or may not be present in the sequence."

(ix) FEATURE:
(A) NAME/KEY: Modified-site
(B) LOCATION: 21
(D) OTHER INFORMATION: /note= "An amino acid selected from Ala, Ser, Thr, Pro or Gly."

(ix) FEATURE:
(A) NAME/KEY: Modified-site
(B) LOCATION: 36
(D) OTHER INFORMATION: /note= "An amino acid selected from His, Arg, or Lys. Xaa may or may not be present in the sequence."

(ix) FEATURE:
(A) NAME/KEY: Modified-site
(B) LOCATION: 37
(D) OTHER INFORMATION: /note= An amino acid selected from His, Arg, or Lys. Xaa may or may not be present in the sequence."

(xi) SEQUENCE DESCRIPTION: SEQ ID NO:2:

Xaa Xaa His Ala Asp Gly Ser Phe Ser Asp Glu Met Asn Thr Ile Leu
1               5                   10                  15

Asp Asn Leu Ala Xaa Arg Asp Phe Ile Asn Trp Leu Ile Gln Thr Lys
                20                  25                  30

Ile Thr Asp Xaa Xaa
            35

(2) INFORMATION FOR SEQ ID NO:3:

(i) SEQUENCE CHARACTERISTICS:
    (A) LENGTH: 33 amino acids
    (B) TYPE: amino acid
    (C) STRANDEDNESS:
    (D) TOPOLOGY: unknown (ii) MOLECULE TYPE: peptide (xi) SEQUENCE DESCRIPTION: SEQ ID NO:3:

His Ala Asp Gly Ser Phe Ser Asp Glu Met Asn Thr Ile Leu Asp Asn
1               5                   10                  15

Leu Ala Thr Arg Asp Phe Ile Asn Trp Leu Ile Gln Thr Lys Ile Thr
                20                  25                  30

Asp (2) INFORMATION FOR SEQ ID NO:4:

(i) SEQUENCE CHARACTERISTICS:
    (A) LENGTH: 33 amino acids
    (B) TYPE: amino acid
    (C) STRANDEDNESS:
    (D) TOPOLOGY: unknown (ii) MOLECULE TYPE: peptide (xi) SEQUENCE DESCRIPTION: SEQ ID NO:4:

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp